(12) United States Patent
Zhu et al.

(10) Patent No.: US 7,728,026 B2
(45) Date of Patent: Jun. 1, 2010

(54) 2-SUBSTITUTED-1 H-BENZIMIDAZILE-4-CARBOXAMIDES ARE PARP INHIBITORS

(75) Inventors: Gui-Dong Zhu, Gurnee, IL (US); Virajkumar B. Gandhi, Park City, IL (US); Jianchun Gong, Deerfield, IL (US); Thomas D. Penning, Elmhurst, IL (US); Vincent L. Giranda, Gurnee, IL (US); Sheela Thomas, Libertyville, IL (US)

(73) Assignee: Abbott Laboratories, Inc., Abbott Park, IL (US)

( * ) Notice: Subject to any disclaimer, the term of this patent is extended or adjusted under 35 U.S.C. 154(b) by 561 days.

(21) Appl. No.: 11/401,635

(22) Filed: Apr. 11, 2006

(65) Prior Publication Data

US 2006/0229351 A1   Oct. 12, 2006

Related U.S. Application Data

(60) Provisional application No. 60/670,205, filed on Apr. 11, 2005.

(51) Int. Cl.
  *A61K 31/4184* (2006.01)
  *C07D 235/04* (2006.01)
(52) U.S. Cl. .................. 514/394; 548/300.1; 548/302.7; 548/304.4; 548/309.7; 514/385
(58) Field of Classification Search ............... 548/300.1, 548/302.7, 304.4, 309.7; 514/385, 394
See application file for complete search history.

(56) References Cited

U.S. PATENT DOCUMENTS

| | | | |
|---|---|---|---|
| 3,864,385 A | 2/1975 | Felt et | |
| 4,093,726 A | 6/1978 | Winn et al. | |
| 6,372,736 B1 | 4/2002 | Kemp et al. | |
| 6,448,271 B1 | 9/2002 | Lubisch et al. | |
| 6,509,365 B1 | 1/2003 | Lubisch et al. | |
| 6,696,437 B1 * | 2/2004 | Lubisch et al. | 514/217.09 |
| 6,737,421 B1 * | 5/2004 | Lubish et al. | 514/218 |
| RE39,608 E | 5/2007 | Lubisch et | |
| 7,462,724 B2 * | 12/2008 | Penning et al. | 548/310.7 |
| 7,550,603 B2 | 6/2009 | Zhu et al. | |
| 2003/0100582 A1 | 5/2003 | Sircar et al. | |
| 2006/0229289 A1 | 10/2006 | Zhu et al. | |
| 2007/0179136 A1 | 8/2007 | Penning et al. | |
| 2007/0259937 A1 | 11/2007 | Giranda et al. | |
| 2007/0265324 A1 | 11/2007 | Wernet et al. | |
| 2009/0030016 A1 | 1/2009 | Ghandhi et al. | |

FOREIGN PATENT DOCUMENTS

| DE | 3522230 A1 | 1/1987 |
|---|---|---|
| DE | 3830060 A1 | 3/1990 |
| DE | 19916460 A1 | 10/2000 |
| DE | 10021468 A1 | 11/2001 |
| DE | 19920936 A1 | 11/2001 |
| GB | 1354554 A | 6/1974 |
| JP | 2002-141067 A1 | 5/2002 |
| WO | 97/04771 A1 | 2/1997 |
| WO | 98/39343 A1 | 9/1998 |
| WO | 00/29384 A1 | 5/2000 |
| WO | 00/32579 A1 | 6/2000 |
| WO | 00/64878 | 11/2000 |
| WO | 01/21615 A1 | 3/2001 |
| WO | 01/21634 A1 | 3/2001 |
| WO | 01/82877 A2 | 11/2001 |
| WO | 02/68407 A1 | 6/2002 |
| WO | 03/020698 A2 | 3/2003 |
| WO | 03/094861 A2 | 11/2003 |
| WO | WO 03/106430 A1 | 12/2003 |
| WO | 2004/054515 A2 | 7/2004 |
| WO | 2004/065370 A1 | 8/2004 |
| WO | 2004/096793 A1 | 11/2004 |
| WO | 2004/098494 A2 | 11/2004 |
| WO | 00/26192 | 5/2005 |
| WO | WO 2005/044988 A2 | 5/2005 |
| WO | WO 2006/023400 A2 | 2/2006 |

OTHER PUBLICATIONS

Skalitzky et al (2003): STN International HCAPLUS database, (Columbus, Ohio), Accession No. 2003:1006960.*
PCT Search Report from PCT/US2006/013366 mailed on Aug. 18, 2006.
Alexy, et al., "Inhibition ADP-Evoked Platelet Aggregation by Selected Poly(ADP-Ribose) Polymerase Inhibitors", Journal Cardiovascular of Pharmacol 43(3), 423-431 (2004).
Burkart, V., "Mice lacking the poly (ADP-ribose) polymerase gene are resistant to pancreatic beta-cell destructin and diabetes development induced by streptozocin", Nat. Med., 5(3):314-319 (1999).

(Continued)

*Primary Examiner*—Golam M Shameem
(74) *Attorney, Agent, or Firm*—Susan L. Steele

(57) ABSTRACT

Compounds of Formula (I)

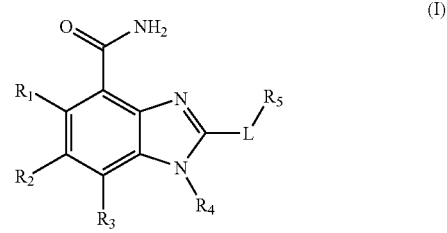

inhibit the PARP enzyme and are useful for treating a disease or a disorder associated with PARP. Also disclosed are pharmaceutical compositions comprising compounds of Formula (I), method of treatment comprising compounds of Formula (I), and methods of inhibiting the PARP enzyme comprising compound of Formula (I).

8 Claims, No Drawings

OTHER PUBLICATIONS

Chen, et al., "Potentiation of the antitumor activity of cisplatin in mice by 3-aminobenzamide and nicotinamide", Cancer Chem. Pharm., 22:303-307 (1966).

Cuzzocrea, "Protective effects of 3-aminobenzamide, an Inhibitor of poly (ADP-ribose) synthase in a carrageenan-induced model of local inflammation", Eur. J. of Pharm., 342:67-76 (1998).

Ehrlich, W., et al., "Inhibition of the induction of collagenase by interleukin-1 in cultured rabbit synovial fibroblasts after treatment with the poly(ADP-ribose)-polymerase inhibitor 3-aminobenzamide", Rheumatol Int., 15:171-172 (1995).

Gilchrist, et al., "Cyclisation of ortho-Substituted N-Arylbenzimidoyl Nitrenes. Part 2. Preferential Cyclisatlons at an ortho-Position Bearin a Methoxycarbonyl Group", Journal of Chem. Society, Perkin Transactions 1, GB, Chemical Society, Letchworth, 2303-2307 (1979).

Griffin, et al., "Resistance modifying agents 3. Novel benzimidazole and quinazolinone inhibitors of the DNA repair enzyme poly(ADP-ribose)polymerase," Pharmaceutical Sciences, 2(1), 43-47 (1996).

Kröger, H., "Synergistic Effects of Thalidomide and Poly(ADP-Ribose) Polymerase Inhibition of Type II Collagen-Induced Arthritis in Mice", Inflammation, 20(2):203-215 (1996).

Poste, et al., "Methods in Cell Biology," Academic Press, Inc., vol. XIV, pp. 33-71, 1976.

Szabo, C., et al., "Protection against peroxynitrite-induced fibroblast injury and arthritis development by inhibition of poly(ADP-ribose) synthase", Proc. Natl., Acad. Sci. USA, 95:38673872 (1998).

Thiemermann, C., et al., "Inhibition of the activity of poly (ADP ribose) synthhetase reduces ischemia-reperfusion injury in the heart and skeletal muscle", Proc. Natl. Acad. Sci. USA, 94:679-683 (1997).

Welkin, D., et al., "Immunosuppressive Activities of 6(5H)-Phenanthridinone, A New Poly(ADP-Ribose)Polymerase Inhibitor", Int. J. Immunopharmac., 17(4)265-271 (1995).

White, et al., "Potentiation of cytotoxic drug activity in human tumore cell lines, by amine-substituted 2-arylbenzimioazol-4carboxamide PARP-1 inhibitors", Bioorganic & Medicinal Chemistry Letters, 14(10), 2433-2437 (2004).

Co-pending U.S. Appl. No. 09/830,992.
Co-pending U.S. Appl. No. 11/536,994.
Co-pending U.S. Appl. No. 11/623,996.
Co-pending U.S. Appl. No. 11/830,318.
Co-pending U.S. Appl. No. 11/970,828.
Co-pending U.S. Appl. No. 12/058,478.
Co-pending U.S. Appl. No. 12/116,823.
Co-pending U.S. Appl. No. 12/117,452.
Co-pending U.S. Appl. No. 12/173,213.
Co-pending U.S. Appl. No. 12/413,834.

* cited by examiner

2-SUBSTITUTED-1 H-BENZIMIDAZILE-4-CARBOXAMIDES ARE PARP INHIBITORS

This application claims priority from U.S. Provisional Patent Application Ser. No. 60/670,205, filed Apr. 11, 2005, incorporated herein by reference.

TECHNICAL FIELD

The present invention relates to 2-substituted-1H-benzimidazole-4-carboxamides, their preparation, and their use as inhibitors of the enzyme poly(ADP-ribose)polymerase for the preparation of drugs.

BACKGROUND

Poly(ADP-ribose)polymerase (PARP) or poly(ADP-ribose)synthase (PARS) has an essential role in facilitating DNA repair, controlling RNA transcription, mediating cell death, and regulating immune response. These actions make PARP inhibitors targets for a broad spectrum of disorders. PARP inhibitors have demonstrated efficacy in numerous models of disease, particularly in models of ischemia reperfusion injury, inflammatory disease, degenerative diseases, protection from adverse effects of cytoxic compounds, and the potentiation of cytotoxic cancer therapy. PARP has also been indicated in retroviral infection and thus inhibitors may have use in antiretroviral therapy. PARP inhibitors have been efficacious in preventing ischemia reperfusion injury in models of myocardial infarction, stroke, other neural trauma, organ transplantation, as well as reperfusion of the eye, kidney, gut and skeletal muscle. Inhibitors have been efficacious in inflammatory diseases such as arthritis, gout, inflammatory bowel disease, CNS inflammation such as MS and allergic encephalitis, sepsis, septic shock, hemmorhagic shock, pulmonary fibrosis, and uveitis. PARP inhibitors have also shown benefit in several models of degenerative disease including diabetes (as well as complications) and Parkinsons disease. PARP inhibitors can ameliorate the liver toxicity following acetominophen overdose, cardiac and kidney toxicities from doxorubicin and platinum based antineoplastic agents, as well as skin damage secondary to sulfur mustards. In various cancer models, PARP inhibitors have been shown to potentiate radiation and chemotherapy by increasing apoptosis of cancer cells, limiting tumor growth, decreasing metastasis, and prolonging the survival of tumor-bearing animals.

The present invention describes the finding that 2-substituted-1H-benzimidazole-4-carboxamides are potent PARP inhibitors.

SUMMARY OF THE INVENTION

In one embodiment, the present invention provides compounds of Formula (I)

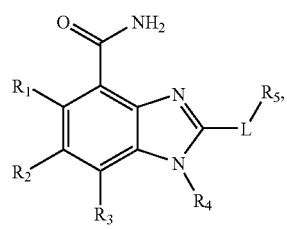

(I)

or a therapeutically acceptable salt thereof, wherein $R_1$, $R_2$, and $R_3$ are independently selected from the group consisting of hydrogen, alkenyl, alkoxy, alkoxycarbonyl, alkyl, alkynyl, cyano, haloalkoxy, haloalkyl, halogen, hydroxy, hydroxyalkyl, nitro, $NR_AR_B$, and $(NR_AR_B)$carbonyl;

L is selected from the group consisting of alkenylene, alkylene, alkynylene, cycloalkylene, and spiroheterocycle;

$R_4$ is selected from the group consisting of hydrogen, alkoxyalkyl, alkyl, heterocyclealkyl, hydroxyalkyl, and $(NR_AR_B)$alkyl;

$R_5$ is selected from the group consisting of heteroaryl, heteroarylalkoxy, heteroaryloxy, heteroarylthio, heteroarylalkylthio; heterocycle, heterocyclealkoxy, heterocyclealkylthio, heterocycleoxy, heterocyclethio, and $NR_CR_D$;

$R_A$ and $R_B$ are independently selected from the group consisting of hydrogen, alkyl, and alkycarbonyl;

$R_C$ and $R_D$ are independently selected from the group consisting of hydrogen, alkyl, alkycarbonyl, alkoxycarbonyl, alkoxycarbonylcycloalkyl, alkoxycarbonylaryl, arylalkyl, arylalkoxy, arylalkoxycarbonyl, cycloalkyl, cycloalkylalkyl, heteroaryl, heteroarylalkyl, heterocycle, heterocyclealkyl, $(NR_ER_F)$alkyl, $(NR_ER_F)$carbonyl, and $(NR_ER_F)$sulfonyl; and $R_E$ and $R_F$ are independently selected from the group consisting of hydrogen, alkyl, aryl, arylalkyl, cycloalkyl, cycloalkylalkyl, heteroaryl, heteroarylalkyl, heterocycle, and heterocyclealkyl.

DETAILED DESCRIPTION OF THE INVENTION

In another embodiment, the present invention provides compounds of Formula (I) wherein $R_1$, $R_2$, and $R_3$ are independently selected from the group consisting of hydrogen, alkyl, and halogen; $R_4$ is selected from the group consisting of hydrogen and alkyl; L is selected from the group consisting of alkylene and cycloalkylene; $R_5$ is selected from the group consisting of heteroaryl, heterocycleoxy, and $NR_CR_D$; $R_C$ and $R_D$ are independently selected from the group consisting of hydrogen, alkyl, alkycarbonyl, arylalkyl, cycloalkyl, cycloalkylalkyl, heteroarylalkyl, $(NR_ER_F)$carbonyl, and $(NR_ER_F)$sulfonyl; and $R_E$ and $R_F$ are independently selected from the group consisting of hydrogen, alkyl, and cycloalkyl.

In another embodiment, the present invention provides compounds of Formula (I) wherein L is alkylene; and $R_1$, $R_2$, $R_3$, $R_4$, and $R_5$ are as defined in Formula (I).

In another embodiment, the present invention provides compounds of Formula (I) wherein L is alkylene; $R_5$ is $NR_CR_D$; and $R_C$, $R_D$, $R_1$, $R_2$, $R_3$, and $R_4$ are as defined in Formula (I).

In another embodiment, the present invention provides compounds of Formula (I) wherein $R_1$, $R_2$, and $R_3$ are independently selected from the group consisting of hydrogen, alkyl, and halogen; $R_4$ is hydrogen; L is alkylene; $R_5$ is $NR_CR_D$; $R_C$ and $R_D$ are independently selected from the group consisting of hydrogen, alkyl, alkycarbonyl, arylalkyl, cycloalkyl, cycloalkylalkyl, $(NR_ER_F)$carbonyl, and $(NR_ER_F)$sulfonyl; and $R_E$ and $R_F$ are independently selected from the group consisting of hydrogen, alkyl, and cycloalkyl.

In another embodiment, the present invention provides compounds of Formula (I) wherein $R_1$, $R_2$, and $R_3$ are independently selected from the group consisting of hydrogen, alkyl, and halogen; $R_4$ is hydrogen; L is alkylene; $R_5$ is $NR_CR_D$; $R_C$ is hydrogen; and $R_D$ is heteroarylalkyl.

In another embodiment, the present invention provides compounds of Formula (I) wherein $R_1$, $R_2$, and $R_3$ are independently selected from the group consisting of hydrogen, alkyl, and halogen; $R_4$ is hydrogen; L is alkylene; $R_5$ is $NR_CR_D$; $R_C$ is hydrogen; and $R_D$ is heteroarylalkyl wherein heteroaryl of the heteroarylalkyl is pyridinyl.

In another embodiment, the present invention provides compounds of Formula (I) wherein L is alkylene; $R_5$ is heteroaryl; and $R_1$, $R_2$, $R_3$, and $R_4$ are as defined in Formula (I).

In another embodiment, the present invention provides compounds of Formula (I) wherein $R_1$, $R_2$, and $R_3$ are independently selected from the group consisting of hydrogen, alkyl, and halogen; $R_4$ is hydrogen; L is alkylene; and $R_5$ is heteroaryl.

In another embodiment, the present invention provides compounds of Formula (I) wherein $R_1$, $R_2$, and $R_3$ are independently selected from the group consisting of hydrogen, alkyl, and halogen; $R_4$ is hydrogen; L is alkylene; and $R_5$ is heteroaryl wherein the heteroaryl is pyrazolyl.

In another embodiment, the present invention provides compounds of Formula (I) wherein L is alkylene; $R_5$ is heterocycleoxy; and $R_1$, $R_2$, $R_3$, and $R_4$ are as defined in Formula (I).

In another embodiment, the present invention provides compounds of Formula (I) wherein $R_1$, $R_2$, and $R_3$ are independently selected from the group consisting of hydrogen, alkyl, and halogen; $R_4$ is hydrogen; L is alkylene; $R_5$ is heterocycleoxy.

In another embodiment, the present invention provides compounds of Formula (I) wherein $R_1$, $R_2$, and $R_3$ are independently selected from the group consisting of hydrogen, alkyl, and halogen; $R_4$ is hydrogen; L is alkylene; $R_5$ is heterocycleoxy wherein heterocycle of the heterocycleoxy is piperidinyl optionally substituted with 1 substituent selected from the group consisting of alkyl and cycloalkyl.

In another embodiment, the present invention provides compounds of Formula (I) wherein L is cycloalkylene; and $R_1$, $R_2$, $R_3$, $R_4$, and $R_5$ are as defined in Formula (I).

In another embodiment, the present invention provides compounds of Formula (I) wherein L is cycloalkylene; $R_5$ is $NR_CR_D$; and $R_C$, $R_D$, $R_1$, $R_2$, $R_3$, and $R_4$ are as defined in Formula (I).

In another embodiment, the present invention provides compounds of Formula (I) wherein $R_1$, $R_2$, and $R_3$ are independently selected from the group consisting of hydrogen, alkyl, and halogen; $R_4$ is hydrogen; L is cycloalkylene; $R_5$ is $NR_CR_D$; and $R_C$ and $R_D$ are independently selected from the group consisting of hydrogen, alkyl, arylalkyl, cycloalkyl, and cycloalkylalkyl.

In another embodiment, the present invention provides compounds of Formula (I) wherein $R_1$, $R_2$, and $R_3$ are independently selected from the group consisting of hydrogen, alkyl, and halogen; $R_4$ is hydrogen; L is cycloalkylene wherein A is selected from the group consisting of cyclopropyl and cyclobutyl; $R_5$ is $NR_CR_D$; and $R_C$ and $R_D$ are independently selected from the group consisting of hydrogen, alkyl, arylalkyl, cycloalkyl, and cycloalkylalkyl.

In another embodiment, the present invention provides compounds of Formula (I) wherein $R_1$, $R_2$, and $R_3$ are independently selected from the group consisting of hydrogen, alkyl, and halogen; $R_4$ is hydrogen; L is cycloalkylene; $R_5$ is $NR_CR_D$; $R_C$ is hydrogen; and $R_D$ heteroarylalkyl.

In another embodiment, the present invention provides compounds of Formula (I) wherein $R_1$, $R_2$, and $R_3$ are independently selected from the group consisting of hydrogen, alkyl, and halogen; $R_4$ is hydrogen; L is cycloalkylene wherein A is selected from the group consisting of cyclopropyl and cyclobutyl; $R_5$ is $NR_CR_D$; $R_C$ is hydrogen; and $R_D$ heteroarylalkyl wherein heteroaryl of the heteroarylalkyl is pyridinyl.

In another embodiment, the present invention provides a pharmaceutical composition comprising a compound of Formula (I), or a therapeutically acceptable salt thereof, in combination with a therapeutically acceptable carrier.

In another embodiment, the present invention provides a method of inhibiting PARP in a mammal in recognized need of such treatment comprising administering to the mammal a therapeutically acceptable amount of a compound of Formula (I) or a therapeutically acceptable salt thereof.

In another embodiment, the present invention provides a method of treating cancer in a mammal in recognized need of such treatment comprising administering to the mammal a therapeutically acceptable amount of a compound of Formula (I) or a therapeutically acceptable salt thereof.

In another embodiment, the present invention provides a method of treating leukemia, colon cancer, glioblastomas, lymphomas, melanomas, carcinomas of the breast, or cervical carcinomas in a mammal in recognized need of such treatment comprising administering to the mammal a therapeutically acceptable amount of a compound of Formula (I) or a therapeutically acceptable salt thereof.

In another embodiment, the present invention provides a method of potentiation of cytotoxic cancer therapy in a mammal in recognized need of such treatment comprising administering to the mammal a therapeutically acceptable amount of a compound of Formula (I) or a therapeutically acceptable salt thereof.

In another embodiment, the present invention provides a method of treating ischemia reperfusion injury associated with, but not limited to, heart failure, myocardial infarction, stroke, other neural trauma, and organ transplantation, in a mammal in recognized need of such treatment comprising administering to the mammal a therapeutically acceptable amount of a compound of Formula (I) or a therapeutically acceptable salt thereof.

In another embodiment, the present invention provides a method of reperfusion including, but not limited to, reperfusion of the eye, kidney, gut and skeletal muscle, in a mammal in recognized need of such treatment comprising administering to the mammal a therapeutically acceptable amount of a compound of Formula (I) or a therapeutically acceptable salt thereof.

In another embodiment, the present invention provides a method of treating inflammatory diseases including, but not limited to, arthritis, gout, inflammatory bowel disease, CNS inflammation, multiple sclerosis, allergic encephalitis, sepsis, septic shock, hemmorhagic shock, pulmonary fibrosis, and uveitis in a mammal in recognized need of such treatment comprising administering to the mammal a therapeutically acceptable amount of a compound of Formula (I) or a therapeutically acceptable salt thereof.

In another embodiment, the present invention provides a method of treating immunological diseases or disorders such as rheumatoid arthritis and septic shock in a mammal in recognized need of such treatment comprising administering to the mammal a therapeutically acceptable amount of a compound of Formula (I) or a therapeutically acceptable salt thereof.

In another embodiment, the present invention provides a method of treating degenerative disease including, but not limited to, diabetes and Parkinsons disease, in a mammal in recognized need of such treatment comprising administering to the mammal a therapeutically acceptable amount of a compound of Formula (I) or a therapeutically acceptable salt thereof.

In another embodiment, the present invention provides a method of treating hypoglycemia in a mammal in recognized need of such treatment comprising administering to the mammal a therapeutically acceptable amount of a compound of Formula (I) or a therapeutically acceptable salt thereof.

In another embodiment, the present invention provides a method of treating retroviral infection in a mammal in recognized need of such treatment comprising administering to the mammal a therapeutically acceptable amount of a compound of Formula (I) or a therapeutically acceptable salt thereof.

In another embodiment, the present invention provides a method of treating liver toxicity following acetaminophen overdose in a mammal in recognized need of such treatment comprising administering to the mammal a therapeutically acceptable amount of a compound of Formula (I) or a therapeutically acceptable salt thereof.

In another embodiment, the present invention provides a method of treating cardiac and kidney toxicities from doxorubicin and platinum based antineoplastic agents in a mammal in recognized need of such treatment comprising administering to the mammal a therapeutically acceptable amount of a compound of Formula (I) or a therapeutically acceptable salt thereof.

In another embodiment, the present invention provides a method of treating skin damage secondary to sulfur mustards in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for inhibiting the PARP enzyme in a mammal in recognized need of such treatment.

In another embodiment, the present invention provides a use of a compound of Formula (I), or a therapeutically acceptable salt thereof, to prepare a medicament for inhibiting tumor growth in a mammal in recognized need of such treatment.

In another embodiment, the present invention provides a use of a compound of Formula (I), or a therapeutically acceptable salt thereof, to prepare a medicament for treating cancer in a mammal in recognized need of such treatment.

In another embodiment, the present invention provides a use of a compound of Formula (I), or a therapeutically acceptable salt thereof, to prepare a medicament for treating leukemia, colon cancer, glioblastomas, lymphomas, melanomas, carcinomas of the breast, or cervical carcinomas in a mammal in recognized need of such treatment.

In another embodiment, the present invention provides a use of a compound of Formula (I), or a therapeutically acceptable salt thereof, to prepare a medicament for potentiation of cytotoxic cancer therapy in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating ischemia reperfusion injury associated with, but not limited to, heart failure, myocardial infarction, stroke, other neural trauma, and organ transplantation, in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating reperfusion including, but not limited to, reperfusion of the eye, kidney, gut and skeletal muscle, in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating inflammatory diseases including, but not limited to, arthritis, gout, inflammatory bowel disease, CNS inflammation, multiple sclerosis, allergic encephalitis, sepsis, septic shock, hemmorhagic shock, pulmonary fibrosis, and uveitis in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating immunological diseases or disorders such as rheumatoid arthritis and septic shock in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating degenerative disease including, but not limited to, diabetes and Parkinsons disease, in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating hypoglycemia in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating retroviral infection in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating liver toxicity following acetaminophen overdose in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating cardiac and kidney toxicities from doxorubicin and platinum based antineoplastic agents in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating skin damage secondary to sulfur mustards in a mammal in recognized need of such treatment comprising administering to the mammal a therapeutically acceptable amount of a compound of Formula (I) or a therapeutically acceptable salt thereof.

Definitions

All patents, patent applications, and literature references cited in the specification are herein incorporated by reference in their entirety. In the case of inconsistencies, the present disclosure, including definitions, will prevail.

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of from 2 to 10 carbon atoms containing at least one double bond. The alkenylene is optionally substituted with 1 or 2 substituents selected from the group consisting of aryl and hydroxy. Representative examples of alkenylene include, but are not limited to, —CH=CH—, —CH=CH$_2$CH$_2$—, —CH=CH$_2$CH (Ph)—, —CH=C(CH$_3$)CH$_2$—, and —CH=C(CH$_3$)CH$_2$CH(OH)CH$_2$—.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain hydrocarbon of from 1 to 10 carbon atoms. The alkylene is optionally substituted with 1 or 2 substituents selected from the group consisting of aryl and hydroxy. Representative examples of alkylene include, but are not limited to, —CH$_2$—, —CH(CH$_3$)—, —C(CH$_3$)$_2$—, —CH(CH$_2$Ph)—, —CH$_2$CH$_2$—, —CH$_2$CH$_2$CH$_2$—, —CH(CH$_3$)CH$_2$CH(Ph)CH$_2$—, —CH$_2$CH(CH$_3$)CH$_2$—, and —CH(CH$_3$)CH$_2$CH$_2$—.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkylthioalkyl" as used herein, means an alkylthio group, as defined herein, appended to the parent molecular moiety through an alkyl group, as defined herein. Representative examples of alkylthioalkyl include, but are not limited, methylthiomethyl and 2-(ethylthio)ethyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkynylene" means a divalent group derived from a straight or branched chain hydrocarbon of from 2 to 10 carbon atoms containing at least one triple bond. The alkynylene is optionally substituted with 1 or 2 substituents selected from the group consisting of aryl and hydroxy. Representative examples of alkynylene include, but are not limited to, —C≡CCH$_2$—, —CH$_2$C≡CCH$_2$—, —CH(CH$_2$Ph)CH$_2$C≡CCH$_2$—, —CH(CH$_2$OH)CH$_2$C≡CCH$_2$—, —C≡CCH$_2$—, and —C≡CCH(CH$_3$)CH$_2$—.

The term "aryl," as used herein, means a phenyl group or a bicyclic aryl ring. The aryl groups of the present invention can be attached to the parent molecular moiety through any carbon atom within the aryl group while maintaining the proper valence. The bicyclic aryl ring consists of the phenyl group fused to a cycloalkyl group or the phenyl group fused to a cycloalkenyl group or the phenyl group fused to another phenyl group (naphthyl). Representative examples of the bicyclic aryl ring include, but are not limited to, 2,3-dihydro-1H-indenyl, 1H-indenyl, naphthyl, 7,8-dihydronaphthalenyl, and 5,6,7,8-tetrahydronaphthalenyl.

The aryl groups of the present invention can be optionally substituted with one, two, three, four, or five substituents independently selected from the group consisting of alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, ethylenedioxy, formyl, haloalkoxy, haloalkyl, halogen, hydroxy, hydroxyalkyl, mercapto, methylenedioxy, nitro, —NZ$_1$Z$_2$, and (NZ$_1$Z$_2$)carbonyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "carbonyl" as used herein, means a —C(O)— group.

The term "carboxy" as used herein, means a —CO$_2$H group.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkenyl" as used herein, means a cyclic hydrocarbon containing from 3 to 8 carbons and containing at least one carbon-carbon double bond formed by the removal of two hydrogens. Representative examples of cycloalkenyl include, but are not limited to, 2-cyclohexen-1-yl, 3-cyclohexen-1-yl, 2,4-cyclohexadien-1-yl and 3-cyclopenten-1-yl.

The term "cycloalkyl" as used herein, means a saturated cyclic hydrocarbon group containing from 3 to 8 carbons, examples of cycloalkyl include cyclopropyl, cyclobutyl, cyclopentyl, cyclohexyl, cycloheptyl, and cyclooctyl.

The cycoalkyl groups of the present invention are optionally substituted with 1, 2, 3, or 4 substituents selected from alkenyl, alkoxy, alkoxyalkoxy, alkoxyalkyl, alkoxycarbonyl, alkyl, alkylcarbonyl, alkylcarbonyloxy, alkylthio, alkynyl, carboxy, cyano, haloalkoxy, haloalkyl, halogen, hydroxy, hydroxyalkyl, mercapto, oxo, —NZ$_1$Z$_2$, and (NZ$_1$Z$_2$)carbonyl.

The term "cycloalkylene" as used herein, means

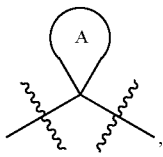

wherein A is cycloalkyl or cycloalkyl fused to phenyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "ethylenedioxy" as used herein, means a —O(CH$_2$)$_2$O— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl" as used herein, means a —C(O)H group.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl ring or a bicyclic heteroaryl ring. The monocyclic heteroaryl ring is a 5 or 6 membered ring. The 5 membered ring has two double bonds and contains one, two, three or four heteroatoms independently selected from the group consisting of N, O, and S. The 6 membered ring has three double bonds and contains one, two, three or four heteroatoms independently selected from the group consisting of N, O, and S. The bicyclic heteroaryl ring consists of the 5 or 6 membered heteroaryl ring fused to a phenyl group or the 5 or 6 membered heteroaryl ring fused to a cycloalkyl group or the 5 or 6 membered heteroaryl ring fused to a cycloalkenyl group or the 5 or 6 membered heteroaryl ring fused to another 5 or 6 membered heteroaryl ring. Nitrogen heteroatoms contained within the heteroaryl may be optionally oxidized to the N-oxide or optionally protected with a nitrogen protecting group known to those of skill in the art. The heteroaryl is connected to the parent molecular moiety through any carbon atom or any nitrogen atom contained within the heteroaryl. Representative examples of heteroaryl include, but are not limited to, benzothienyl, benzoxadiazolyl, cinnolinyl, 5,6-dihydroisoquinolinyl, 7,8-dihydroisoquinolinyl, 5,6-dihydroquinolinyl, 7,8-dihydroquinolinyl, furopyridinyl, furyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, pyridinium N-oxide, quinolinyl, 5,6,7,8-tetrahydroisoquinolinyl, 5,6,7,8-tetrahydroquinolinyl, tetrazolyl, thiadiazolyl, thiazolyl, thienopyridinyl, thienyl, triazolyl, and triazinyl.

The heteroaryl groups of the present invention are substituted with 0, 1, 2, 3, or 4 substituents independently selected from alkenyl, alkoxy, alkoxyalkoxy, alkoxyalkyl, alkoxycarbonyl, alkoxycarbonylalkyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, nitro, —NZ$_1$Z$_2$, and (NZ$_1$Z$_2$)carbonyl.

The term "heteroarylalkoxy" as used herein, means a heteroaryl group, as defined herein, appended to the parent molecular moiety through an alkoxy group, as defined herein.

The term "heteroarylalkyl" as used herein, means a heteroaryl, as defined herein, appended to the parent molecular moiety through an alkyl group, as defined herein.

The term "heteroarylalkylthio" as used herein, means a heteroarylalkyl group, as defined herein, appended to the parent molecular moiety through a sulfur atom.

The term "heteroaryloxy" as used herein, means a heteroaryl group, as defined herein, appended to the parent molecular moiety through an oxygen atom.

The term "heteroarylthio" as used herein, means a heteroaryl group, as defined herein, appended to the parent molecular moiety through a sulfur atom.

The term "heterocycle" or "heterocyclic" as used herein, means a monocyclic heterocyclic ring or a bicyclic heterocyclic ring. The monocyclic heterocyclic ring consists of a 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. Representative examples of the monocyclic heterocyclic ring include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocyclic ring consists of the monocyclic heterocyclic ring fused to a phenyl group or the monocyclic heterocyclic ring fused to a cycloalkyl group or the monocyclic heterocyclic ring fused to a cycloalkenyl group or the monocyclic heterocyclic ring fused to another monocyclic heterocyclic ring. Representative examples of the bicyclic heterocyclic ring include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl.

The heterocycles of this invention are substituted with 0, 1, 2, or 3 substituents independently selected from alkenyl, alkoxy, alkoxyalkoxy, alkoxyalkyl, alkoxycarbonyl, alkyl, alkylcarbonyl, alkylcarbonyloxy, alkylthio, alkynyl, carboxy, cyano, cycloalkyl, cycloalkylalkyl, formyl, haloalkoxy, haloalkyl, halogen, hydroxy, hydroxyalkyl, mercapto, oxo, —$NZ_1Z_2$, and ($NZ_1Z_2$)carbonyl.

The term "heterocyclealkoxy" as used herein, means a heterocycle group, as defined herein, appended to the parent molecular moiety through an alkoxy group, as defined herein.

The term "heterocyclealkyl" as used herein, means a heterocycle, as defined herein, appended to the parent molecular moiety through an alkyl group, as defined herein.

The term "heterocyclealkylthio" as used herein, means a heterocyclealkyl group, as defined herein, appended to the parent molecular moiety through a sulfur atom. Representative examples of heterocyclealkylthio include, but are not limited to, 2-pyridin-3-ylethythio, 3-quinolin-3-ylpropythio, and 5-pyridin-4-ylpentylthio.

The term "heterocycleoxy" as used herein, means a heterocycle group, as defined herein, appended to the parent molecular moiety through an oxygen atom. Representative examples of heterocycleoxy include, but are not limited to, pyridin-3-yloxy and quinolin-3-yloxy.

The term "heterocyclethio" as used herein, means a heterocycle group, as defined herein, appended to the parent molecular moiety through a sulfur atom.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "methylenedioxy" as used herein, means a —$OCH_2O$— group wherein the oxygen atoms of the methylenedioxy are attached to the parent molecular moiety through two adjacent carbon atoms.

The term "nitro" as used herein, means a —$NO_2$ group.

The term "$NR_AR_B$" as used herein, means two groups, $R_A$ and $R_B$, which are appended to the parent molecular moiety through a nitrogen atom. $R_A$ and $R_B$ are each independently selected from the group consisting of hydrogen, alkyl, and alkylcarbonyl. Representative examples of $NR_AR_B$ include, but are not limited to, amino, methylamino, acetylamino, and acetylmethylamino.

The term "($NR_AR_B$)alkyl" as used herein, means a $NR_AR_B$ group, as defined herein, appended to the parent molecular moiety through an alkyl group, as defined herein. Representative examples of ($NR_AR_B$)alkyl include, but are not limited to, 2-(amino)ethyl, 3-(methylamino)propyl, 4-(dimethylamino)butyl, and 5-(ethylmethylamino)pentyl.

The term "($NR_AR_B$)carbonyl" as used herein, means a $NR_AR_B$ group, as defined herein, appended to the parent molecular moiety through a carbonyl group, as defined herein. Representative examples of ($NR_AR_B$)carbonyl include, but are not limited to, aminocarbonyl, (methylamino)carbonyl, (dimethylamino)carbonyl, and (ethylmethylamino)carbonyl.

The term "$NR_CR_D$" as used herein, means two groups, $R_C$ and $R_D$, which are appended to the parent molecular moiety through a nitrogen atom. $R_C$ and $R_D$ are each independently selected from the group consisting of hydrogen, alkyl, alkycarbonyl, arylalkyl, cycloalkyl, cycloalkylalkyl, heteroaryl, heteroarylalkyl, heterocycle, heterocyclealkyl, ($NR_ER_F$)alkyl, ($NR_ER_F$)carbonyl, and ($NR_ER_F$)sulfonyl. Representative examples of $NR_CR_D$ include, but are not limited to, amino, propylamino, butylamino, (2-phenylethyl)amino, isopropylamino, cyclopropylmethylamino, cyclobutylamino, cyclopentylamino, [(cyclopentylamino)carbonyl]amino, [(ethylamino)carbonyl]amino, [(dimethylamino)sulfonyl]amino, (3,5-dimethylbenzyl)amino, dipropylamino, dibutylamino, cyclohexylamino, isobutylamino, bis(cycloproylmethyl)amino, butyl(pentyl)amino, and dimethylamino.

The term "$NR_ER_F$" as used herein, means two groups, $R_E$ and $R_F$, which are appended to the parent molecular moiety through a nitrogen atom. $R_E$ and $R_F$ are each independently selected from the group consisting of hydrogen, alkyl, aryl, arylalkyl, cycloalkyl, cycloalkylalkyl, heteroaryl, heteroarylalkyl, heterocycle, and heterocyclealkyl.

The term "($NR_ER_F$)alkyl" as used herein, means a $NR_ER_F$ group, as defined herein, appended to the parent molecular moiety through an alkyl group, as defined herein.

The term "($NR_ER_F$)carbonyl" as used herein, means a $NR_ER_F$ group, as defined herein, appended to the parent molecular moiety through a carbonyl group, as defined herein.

The term "($NR_ER_F$)sulfonyl" as used herein, means a $NR_ER_F$ group, as defined herein, appended to the parent molecular moiety through a sulfonyl group, as defined herein.

The term "$NZ_1Z_2$" as used herein, means two groups, $Z_1$ and $Z_2$, which are appended to the parent molecular moiety through a nitrogen atom. $Z_1$ and $Z_2$ are each independently selected from the group consisting of hydrogen, alkyl, alkylcarbonyl, and formyl. Representative examples of $NZ_1Z_2$ include, but are not limited to, amino, methylamino, acetylamino, and acetylmethylamino.

The term "($NZ_1Z_2$)carbonyl" as used herein, means a $NZ_1Z_2$ group, as defined herein, appended to the parent molecular moiety through a carbonyl group, as defined herein. Representative examples of (NZ₁Z₂)carbonyl include, but are not limited to, aminocarbonyl, (methylamino)carbonyl, (dimethylamino)carbonyl, and (ethylmethylamino)carbonyl.

The term "oxo" as used herein, means a =O moiety.

The term "spiroheterocycle" as used herein, means

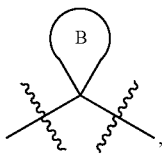

wherein B is a heterocycle or heterocycle fused to phenyl.

The term "sulfonyl" as used herein, means a —SO₂— group.

Compounds of the present invention can exist as stereoisomers, wherein asymmetric or chiral centers are present. Stereoisomers are designated (R) or (S) depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30, hereby incorporated by reference. The present invention contemplates various stereoisomers and mixtures thereof and are specifically included within the scope of this invention. Stereoisomers include enantiomers, diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Compounds of the present invention were named by ACD/ChemSketch version 5.06 (developed by Advanced Chemistry Development, Inc., Toronto, ON, Canada) or were given names which appeared to be consistent with ACD nomenclature.

Determination of Biological Activity

Inhibition of PARP-1

Nicotinamide[2,5',8-3H]adenine dinucleotide and strepavidin SPA beads were purchased from Amersham Biosiences (UK) Recombinant Human Poly(ADP-Ribose) Polymerase (PARP) purified from *E. coli* and 6-Biotin-17-NAD⁺, were purchase from Trevigen, Gaithersburg, Md. NAD⁺, Histone, aminobenzamide, 3-amino benzamide and Calf Thymus DNA (dcDNA) were purchased from Sigma, St. Louis, Mo. Stem loop oligonucleotide containing MCAT sequence was obtained from Qiagen. The oligos were dissoloved to 1 mM in annealing buffer containing 10 mM Tris HCl pH 7.5, 1 mM EDTA, and 50 mM NaCl, incubated for 5 min at 95° C., and followed by annealing at 45° C. for 45 minutes. Histone H1 (95% electrophoretically pure) was purchased from Roche, Indianapolis, Ind. Biotinylated histone H1 was prepared by treating the protein with Sulfo-NHS-LC-Biotin from Pierce Rockford, Ill. The biotinylation reaction was conducted by slowly and intermittently adding 3 equivalents of 10 mM Sulfo-NHS-LC-Biotin to 100 μM Histone H1 in phosphate-buffered saline, pH 7.5, at 4° C. with gentle vortexing over 1 min followed by subsequent 4° C. incubation for 1 hr. Streptavidin coated (FlashPlate Plus) microplates were purchased from Perkin Elmer, Boston, Mass.

PARP-1 assay was conducted in PARP assay buffer containing 50 mM Tris pH 8.0, 1 mM DTT, 4 mM MgCl₂. PARP reactions contained 1.5 μM [³H]-NAD⁺ (1.6 uCi/mmol), 200 nM biotinylated histone H1, 200 nM slDNA, 1 nM PARP enzyme, and a compound of the present invention. Auto reactions utilizing SPA bead-based detection were carried out in 100 μl volumes in white 96 well plates. Reactions were initiated by adding 50 μl of 2×NAD⁺ substrate mixture to 50 μl of 2× enzyme mixture containing PARP and DNA. These reactions were terminated by the addition of 150 μl of 1.5 mM benzamide (~1000-fold over its IC50). 170 μl of the stopped reaction mixtures were transferred to streptavidin Flash Plates, incubated for 1 hr, and counted using a TopCount microplate scintillation counter. An inhibition curve for each tested compound of the present invention was derived from conducting the assay as described herein at different concentrations. Ki values were determined from the inhibition curves and are shown in Table 1.

TABLE 1

| Inhibition of PARP-1 $K_i$ (nM) | | | | |
|---|---|---|---|---|
| 55 | 212 | 56 | 368 | 42 |
| 20 | 10 | 12 | 37 | 7 |
| 751 | 121 | 123 | 36 | 45 |
| 7 | 19 | 9 | 302 | 970 |

Cellular PARP Assay:

C41 cells were treated with a compound of the present invention for 30 minutes in 96 well plate. PARP was then activated by damaging DNA with 1 mM H₂O₂ for 10 minutes. The cells were then washed with ice-cold PBS once and fixed with pre-chilled methanol:acetone (7:3) at −20° C. for 10 minutes. After air-drying, the plates were rehydrated with PBS and blocked 5% non-fat dry milk in PBS-tween (0.05%) (blocking solution) for 30 minutes at room temperature. The cells were incubated with anti-PAR antibody 10H (1:50) in Blocking solution at 37° C. for 60 minutes followed by washing with PBS-Tween20 5 times, and incubation with goat anti-mouse fluorescein 5(6)-isothiocyanate-coupled antibody (1:50) and 1 μg/ml 4',6-diamidino-2-phenylindole (DAPI) in blocking solution at 37° C. for 60 minutes. After washing with PBS-Tween20 5 times, the analysis was performed using an fmax Fluorescence Microplate Reader (Molecular Devices, Sunnyvalle, Calif.), set at the excitation wavelength of 490 nm and emission wavelength of 528 nm fluorescein 5 (6)-isothiocyanate (FITC) or the excitation wavelength of 355 nm and emission wavelength of 460 nm (DAPI). The PARP activity (FITC signal) was normalized with cell numbers (DAPI).

The cellular assay measures the formation of poly ADP-ribose by PARP within cells and demonstrates that compounds of the present invention penetrate cell membranes and inhibit PARP in intact cells. The $EC_{50s}$ for representative compounds of the present invention are provided in Table 2.

TABLE 2

| Cellular Activity EC$_{50}$ (nM) | | | | |
|---|---|---|---|---|
| 6 | 14 | 10 | 2 | 2 |
| 4 | 544 | 21 | 3 | |

The data in Table 1 and Table 2 show that compounds of the present invention are PARP inhibitors compounds that penetrate cell membranes and inhibit PARP in intact cells.

As PARP inhibitors, the compounds of the present invention have numerous therapeutic applications related to, ischemia reperfusion injury, inflammatory diseases, degenerative diseases, protection from adverse effects of cytotoxic compounds, and potentiation of cytotoxic cancer therapy. In particular, compounds of the present invention potentiate radiation and chemotherapy by increasing apoptosis of cancer cells, limiting tumor growth, decreasing metastasis, and prolonging the survival of tumor-bearing mammals. Compounds of Formula (I) can treat leukemia, colon cancer, glioblastomas, lymphomas, melanomas, carcinomas of the breast, and cervical carcinomas.

Other therapeutic applications include, but are not limited to, retroviral infection, arthritis, gout, inflammatory bowel disease, CNS inflammation, multiple sclerosis, allergic encephalitis, sepsis, septic shock, hemmorhagic shock, pulmonary fibrosis, uveitis, diabetes, Parkinsons disease, myocardial infarction, stroke, other neural trauma, organ transplantation, reperfusion of the eye, reperfusion of the kidney, reperfusion of the gut, reperfusion of skeletal muscle, liver toxicity following acetominophen overdose, cardiac and kidney toxicities from doxorubicin and platinum based antineoplastic agents, and skin damage secondary to sulfur mustards. (G. Chen et al. Cancer Chemo. Pharmacol. 22 (1988), 303; C. Thiemermann et al., Proc. Natl. Acad. Sci. USA 94 (1997), 679-683 D. Weltin et al. Int. J. Immunopharmacol. 17 (1995), 265-271; H. Kröger et al. Inflammation 20 (1996), 203-215; W. Ehrlich et al. Rheumatol. Int. 15 (1995), 171-172; C. Szabo et al., Proc. Natl. Acad. Sci. USA 95 (1998), 3867-3872; S. Cuzzocrea et al. Eur. J. Pharmacol. 342 (1998), 67-76; V. Burkhart et al., Nature Medicine (1999), 5314-19).

When used in the above or other treatments, a therapeutically effective amount of one of the compounds of the present invention can be employed as a zwitterion or as a pharmaceutically acceptable salt. By a "therapeutically effective amount" of the compound of the invention is meant a sufficient amount of the compound to treat or prevent a disease or disorder ameliorated by a PARP inhibitor at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific compound employed; and like factors well known in the medical arts. For example, it is well within the skill of the art to start doses of the compound at levels lower than those required to achieve the desired therapeutic effect and to gradually increase the dosage until the desired effect is achieved.

By "therapeutically acceptable salt" is meant those salts which are, within the scope of sound medical judgement, suitable for use in contact with the tissues of humans and lower animals without undue toxicity, irritation, allergic response and the like and are commensurate with a reasonable benefit/risk ratio. Therapeutically acceptable salts are well-known in the art. The salts can be prepared in situ during the final isolation and purification of the compounds of the present invention or separately by reacting the free base of a compound of the present invention with a suitable acid. Representative acids include, but are not limited to acetatic, citric, aspartic, benzoic, benzenesulfonic, butyric, fumaric, hydrochloric, hydrobromic, hydroiodic, lactic, maleic, methanesulfonic, pamoic, pectinic, pivalic, propionic, succinic, tartaric, phosphic, glutamic, and p-toluenesulfonic. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained.

The term "therapeutically acceptable carrier," as used herein, means a non-toxic, inert solid, semi-solid or liquid filler, diluent, encapsulating material or formulation auxiliary of any type. Some examples of materials which can serve as therapeutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The present invention provides therapeutically acceptable compositions which comprise compounds of the present invention formulated together with one or more non-toxic therapeutically acceptable carriers. The pharmaceutical compositions can be formulated for oral administration in solid or liquid form, for parenteral injection or for rectal administration.

Compositions for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions can also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

Total daily dose of the compositions of the invention to be administered to a human or other mammal host in single or divided doses may be in amounts, for example, from 0.0001 to 300 mg/kg body weight daily and more usually 1 to 300 mg/kg body weight. The dose, from 0.0001 to 300 mg/kg body, may be given twice a day.

Abbreviations which have been used in the descriptions of the examples that follow are: DMF for N,N-dimethylformamide; DMSO for dimethylsulfoxide; $Et_2O$ for diethyl ether; EtOAc for ethyl acetate; EtOH for ethanol; HPLC for high pressure liquid chromatography; MeOH for methanol; psi for pounds per square inch; TFA for trifluoroacetic acid; THF for tetrahydrofuran, and TMS for trimethylsilane.

The following Examples are intended as an illustration of and not a limitation upon the scope of the invention as defined in the appended claims. The compounds of this invention can be prepared by a variety of synthetic routes.

EXAMPLE 1

2-(1-amino-1-methylethyl)-1H-benzimidazole-4-carboxamide

EXAMPLE 1A benzyl 2-{[2-amino-3-(aminocarbonyl)phenyl]amino}-1,1-dimethyl-2-oxoethylcarbamate 2-{[(Benzyloxy)carbonyl]amino}-2-methylpropanoic acid (5.18 g, 21.83 mmol) in a mixture of pyridine (25 mL) and DMF (25 mL) was treated with 1,1'-carbonyldiimidazole (3.72 g, 22.92 mmol) and heated at 40° C. for 2 hours. 2,3-Diaminobenzamide dihydrochlolide (4.89 g, 21.83 mmol), prepared as described in WO0026192, was added and the mixture was stirred at room temperature overnight. The solvents were removed under vacuum and the residue was partitioned between ethyl acetate and diluted sodium bicarbonate aqueous solution. The formed slightly yellow solid material was collected by filtration, washed with water and ethyl acetate, and dried to give Example 1A. MS (DCI/$NH_3$) m/z 371 (M+H)$^+$.

EXAMPLE 1B benzyl 1-[4-(aminocarbonyl)-1H-benzimidazol-2-yl]-1-methylethylcarbamate Example 1A in acetic acid (100 mL) was heated under reflux for 2 hours, cooled, concentrated, and the residual oil was partitioned between ethyl acetate and sodium bicarbonate aqueous solution. The organic phase was washed with water and concentrated. The residue was purified by flash column chromatography (silica gel, 10-100% EtOAc/hexane) to provide Example 1B (2.2 g, 29%). MS (DCI/$NH_3$) m/z 353 (M+H)$^+$.

EXAMPLE 1C 2-(1-amino-1-methylethyl)-1H-benzimidazole-4-carboxamide

Example 1B (2.2 g, 6.25 mmol) in methanol (30 mL) was treated with 10% Pd/C (230 mg) at room temperature under hydrogen (60 psi) overnight. The mixture was filtered and the filtrate was concentrated. The residue was recrystallized in methanol to give Example 1C (1.2 g, 88%). MS (DCI/$NH_3$) m/z 219 (M+H)$^+$; $^1$H NMR (400 MHz, DMSO-d6): δ 1.51 (s, 6H), 3.31 (br s, 2H), 7.23 (t, J=7.82 Hz, 1H), 7.59 (s, 1H), 7.64 (d, J=7.98 Hz, 1H), 7.77 (d, J=7.36 Hz, 1H), 9.34 (br s, 1H).

EXAMPLE 2

2-[1-methyl-1-(propylamino)ethyl]-1H-benzimidazole-4-carboxamide

Example 1C (75 mg, 0.34 mmol) in 1,2-dichloroethane (3 mL) and DMF (3 mL) was treated with propionaldehyde (60 mg, 1 mmol) at room temperature for 40 minutes. Sodium triacetoxyborohydride (109 mg, 0.52 mmol) and acetic acid (69 μL) were added and the solution was stirred at room temperature overnight. After concentration, the residue was dissolved in a mixture of trifluoroacetic acid and water, filtered through a membrane filter and purified by HPLC (Zorbax C-18, 0.1% TFA/$CH_3CN/H_2O$) to give Example 2 (30 mg, 34%). MS (DCI/$NH_3$) m/z 261 (M+H)$^+$; $^1$H NMR (400 MHz, $CD_3OD$): δ 1.05 (t, 3H), 1.74-1.85 (m, 2H), 1.90 (s, 6H), 3.00-3.10 (m, 2H), 7.43 (t, J=7.98 Hz, 1H), 7.78 (d, J=7.98 Hz, 1H), 8.01 (d, J=7.67 Hz, 1H); Anal. Calcd for $C_{14}H_{20}N_4O$.1.5 TFA: C, 47.33; H, 5.02; N, 12.99. Found: C, 47.50; H, 5.35; N, 13.17.

EXAMPLE 3

2-[1-(butylamino)-1-methylethyl]-1H-benzimidazole-4-carboxamide

The title compound was prepared according to the procedure for Example 2, substituting butyraldehyde for propionaldehyde (40 mg, 42%). MS (DCI/$NH_3$), m/z 275 (M+H)$^+$; $^1$H NMR (400 MHz, $CD_3OD$): δ 0.98 (t, J=7.36 Hz, 3H), 1.38-1.52 (m, 2H), 1.69-1.81 (m, 2H), 1.91 (s, 6H), 3.02-3.13 (m, 2H), 7.43 (t, J=7.82 Hz, 1H), 7.77 (d, J=7.98 Hz, 1H), 8.01 (d, J=7.67 Hz, 1H); Anal. Calcd for $C_{15}H_{22}N_4O$.1.4 TFA: C, 49.26; H, 5.43; N, 12.91. Found: C, 49.41; H, 5.75; N, 13.16.

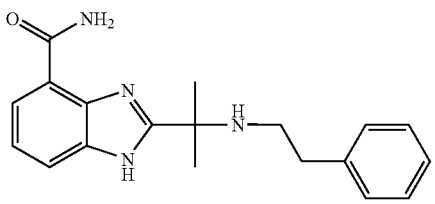

EXAMPLE 4

2-{1-methyl-1-[(2-phenylethyl)amino]ethyl}-1H-benzimidazole-4-carboxamide

The title compound was prepared according to the procedure for Example 2, substituting phenylacetaldehyde for propionaldehyde (20 mg, 18%). MS (DCI/NH$_3$) m/z 323 (M+H)$^+$; $^1$H NMR (400 MHz, CD$_3$OD): δ 1.91 (s, 6H), 3.04-3.13 (m, 2H), 3.32-3.39 (m, 2H), 7.22-7.28 (m, 2H), 7.29-7.33 (m, 1H), 7.33-7.38 (m, 1H), 7.42 (t, J=5.06 Hz, 1H), 7.43-7.47 (m, 1H), 7.77 (d, J=7.98 Hz, 1H), 8.02 (d, J=7.67 Hz, 1H); Anal. Calcd for C$_{19}$H$_{22}$N$_4$O.1.5 TFA: C, 53.55; H, 4.80; N, 11.35. Found: C, 53.85; H, 5.07; N, 11.49.

EXAMPLE 5

2-[1-(isopropylamino)-1-methylethyl]-1H-benzimidazole-4-carboxamide

The title compound was prepared according to the procedure for Example 2, substituting acetone for propionaldehyde (85 mg, 95%). MS (DCI/NH$_3$) m/z 261 (M+H)$^+$; $^1$H NMR (400 MHz, CD$_3$OD): δ 1.30 (d, J=6.75 Hz, 6H), 1.95 (s, 6H), 3.49-3.62 (m, 1H), 7.44 (t, J=7.83 Hz, 1H), 7.79 (d, J=7.98 Hz, 1H), 8.02 (d, J=7.36 Hz, 1H); Anal. Calcd for C$_{14}$H$_{20}$N$_4$O.1.4 TFA: C, 48.05; H, 5.14; N, 13.34. Found: C, 47.72; H, 5.43; N, 13.45.

EXAMPLE 6

2-{1-[(cyclopropylmethyl)amino]-1-methylethyl}-1H-benzimidazole-4-carboxamide The title compound was prepared according to the procedure for Example 2, substituting cyclopropane carboxaldehyde for propionaldehyde (64 mg, 68%).
MS (DCI/NH$_3$) m/z 273 (M+H)$^+$; $^1$H NMR (400 MHz, CD$_3$OD): δ 0.36-0.50 (m, 2H), 0.69-0.82 (m, 2H), 1.04-1.24 (m, 1H), 1.89 (s, 6H), 2.97 (d, J=7.36 Hz, 2H), 7.43 (t, J=7.83 Hz, 1H), 7.77 (d, J=7.06 Hz, 1H), 8.01 (d, J=7.67 Hz, 1H); Anal. Calcd for C$_{15}$H$_{20}$N$_4$O.1.4 TFA: C, 49.49; H, 4.99; N, 12.97. Found: C, 49.61; H, 5.08; N, 13.19.

EXAMPLE 7

2-[1-(cyclobutylamino)-1-methylethyl]-1H-benzimidazole-4-carboxamide

The title compound was prepared according to the procedure for Example 2, substituting cyclobutanone for propionaldehyde (22 mg, 24%). MS (DCI/NH$_3$) m/z 273 (M+H)$^+$; $^1$H NMR (400 MHz, CD$_3$OD): δ 1.84-1.91 (m, 2H), 1.88 (s, 6H), 2.19-2.37 (m, 4H), 3.93-4.09 (m, 1H), 7.44 (t, J=7.98 Hz, 1H), 7.78 (d, J=7.98 Hz, 1H), 8.02 (d, J=7.67 Hz, 1H); Anal. Calcd for C$_{15}$H$_{20}$N$_4$O.1.4 TFA: C, 49.49; H, 4.99; N, 12.97. Found: C, 49.28; H, 5.04; N, 13.00.

EXAMPLE 8

2-[1-(cyclopentylamino)-1-methylethyl]-1H-benzimidazole-4-carboxamide

The title compound was prepared according to the procedure for Example 2, substituting cyclopentanone for propionaldehyde (92 mg, 94%). MS (DCI/NH$_3$), m/z 287 (M+H)$^+$; $^1$H NMR (400 MHz, CD$_3$OD): δ 1.56-1.63 (m, 2H), 1.64-1.72 (m, 2H), 1.73-1.81 (m, 2H), 1.95 (s, 6H), 1.97-2.05 (m, 2H), 3.59-3.84 (m, 1H), 7.44 (t, J=7.82 Hz, 1H), 7.78 (d, J=8.29 Hz, 1H), 8.02 (d, J=7.67 Hz, 1H); Anal. Calcd for C$_{16}$H$_{22}$N$_4$O.1.4 TFA: C, 50.63; H, 5.29; N, 12.56. Found: C, 50.77; H, 5.41; N, 12.81.

EXAMPLE 9

2-(1-{[(cyclopentylamino)carbonyl]amino}-1-methylethyl)-1H-benzimidazole-4-carboxamide Example 1C (75 mg, 0.34 mmol) in DMF (4 mL) was treated with cyclopentyl isocyanate (50 μL) at 0° C. and the mixture was warmed up to room temperature overnight. All volatiles were removed and the residue was dissolved in a mixture of trifluoroacetic acid and water, filtered through a membrane filter and purified by HPLC (Zorbax C-18, 0.1% TFA/CH$_3$CN/H$_2$O) to give Example 9 (98 mg, 87%). MS (DCI/NH$_3$), m/z 330 (M+H)$^+$; $^1$H NMR (500 MHz, CD$_3$OD): δ 1.33-1.43 (m, 2H), 1.51-1.61 (m, 2H), 1.65-1.74 (m, 2H), 1.84 (s, 6H), 1.85-1.90 (m, 2H), 3.65-4.16 (m, 1H), 7.58 (t, J=7.95 Hz, 1H), 7.87 (d, J=7.80 Hz, 1H), 7.98 (d, J=7.49 Hz, 1H); Anal. Calcd for C$_{17}$H$_{23}$N$_5$O$_2$.1.5 TFA: C, 48.00; H, 4.93; N, 13.99. Found: C, 48.38; H, 5.20; N, 14.17.

EXAMPLE 10

2-(1-{[(ethylamino)carbonyl]amino}-1-methylethyl)-1H-benzimidazole-4-carboxamide The title compound was prepared according to the procedure for Example 9, substituting ethyl isocyanate for cyclopentyl isocyanate (86 mg, 87%). MS (DCI/NH$_3$) m/z 290 (M+H)$^+$; $^1$H NMR (500 MHz, DMSO-d6): δ 0.96 (t, J=7.18 Hz, 3H), 1.69 (s, 6H), 2.95 (q, J=7.18 Hz, 2H), 6.08 (s, 1H), 6.49-6.51 (m, 1H), 7.39 (t, J=7.64 Hz, 1H), 7.68 (s, 1H), 7.74 (d, J=8.11 Hz, 1H), 7.86 (d, J=7.49 Hz, 1H), 8.87 (s, 1H); Anal. Calcd for C$_{14}$H$_{19}$N$_5$O$_2$.1.1 TFA: C, 46.91; H, 4.88; N, 16.89. Found: C, 47.22; H, 4.82; N, 16.83.

EXAMPLE 11

2-(1-{[(dimethylamino)sulfonyl]amino}-1-methylethyl)-1H-benzimidazole-4-carboxamide A suspension of Example 1C (75 mg, 0.34 mmol) in methylene chloride (5 mL) was treated with dimethylsulfamoyl chloride (44 μL, 0.41 mmol) and triethylamine (96 μL). Methanol was added until a transparent solution formed (~2 mL). The solution was stirred at room temperature for overnight and was concentrated. The residue was dissolved in a mixture of trifluoroacetic acid and water, filtered through a membrane filter and purified by HPLC (Zorbax C-18, 0.1% TFA/CH$_3$CN/H$_2$O) to give Example 11 (13 mg, 12%). MS (DCI/NH$_3$), m/z 326 (M+H)$^+$; $^1$H NMR (400 MHz, CD$_3$OD):

δ 1.89 (s, 6H), 2.72 (s, 6H), 7.51 (t, J=7.98 Hz, 1H), 7.84 (d, J=7.98 Hz, 1H), 7.98 (d, J=7.67 Hz, 1H).

EXAMPLE 12

2-[1-methyl-1-(1H-pyrazol-1-yl)ethyl]-1H-benzimidazole-4-carboxamide

The title compound was prepared according to the procedures described in Examples 1A and 1B substituting 2-methyl-2-(1H-pyrazol-1-yl)propanoic acid for 2-{[(benzyloxy)carbonyl]amino}-2-methylpropanoic acid (96 mg, 11%). MS (DCI/NH$_3$), m/z 270 (M+H)$^+$; $^1$H NMR (500 MHz, DMSO-d6): δ 2.09 (s, 6H), 6.32 (dd, J=2.50, 1.87 Hz, 1H), 7.31 (t, J=7.80 Hz, 1H), 7.51 (d, J=1.25 Hz, 1H), 7.65 (d, J=0.94 Hz, 1H), 7.67 (d, J=0.94 Hz, 1H), 7.83 (dd, J=7.64, 1.09 Hz, 1H), 7.93 (dd, J=2.50, 0.62 Hz, 1H), 9.05 (s, 1H).

EXAMPLE 13 (A-869659)

2-(1-aminocyclopropyl)-1H-benzimidazole-4-carboxamide

The title compound was prepared according to the procedures described in Examples 1A and 1B substituting 1-aminocyclopropanecarboxylic acid for 2-{[(benzyloxy)carbonyl]amino}-2-methylpropanoic acid (350 mg, 61%). MS (DCI/NH$_3$), m/z 217 (M+H)$^+$; $^1$H NMR (400 MHz, CD$_3$OD): δ 1.65-1.75 (m, 4H), 7.37 (t, J=7.98 Hz, 1H), 7.68 (d, J=7.98 Hz, 1H), 7.97 (d, J=6.75 Hz, 1H).

EXAMPLE 14

2-[1-(isopropylamino)cyclopropyl]-1H-benzimidazole-4-carboxamide

The title compound was prepared according to the procedure for Example 2, substituting Example 13 for Example 1C and acetone for propionaldehyde (70 mg, 78%). (DCI/NH$_3$), m/z 259 (M+H)$^+$; $^1$H NMR (500 MHz, CD$_3$OD): δ 1.40 (d, J=6.71 Hz, 6H), 1.71-1.84 (m, 4H), 3.89-4.01 (m, 1H), 7.41 (t, J=7.78 Hz, 1H), 7.73 (d, J=7.02 Hz, 1H), 7.99 (d, J=6.71 Hz, 1H); Anal. Calcd for C$_{14}$H$_{18}$N$_4$O.1.6 TFA: C, 46.87; H, 4.48; N, 12.71. Found: C, 46.51; H, 4.38; N, 12.89.

EXAMPLE 15

2-[1-(cyclobutylamino)cyclopropyl]-1H-benzimidazole-4-carboxamide

The title compound was prepared according to the procedure for Example 2, substituting Example 13 for Example 1C and cyclobutanone for propionaldehyde (26 mg, 28%). MS (DCI/NH$_3$), m/z 271 (M+H)$^+$; $^1$H NMR (500 MHz, CD$_3$OD): δ 1.65-1.70 (m, 2H), 1.71-1.76 (m, 2H), 1.79-1.94 (m, 2H), 2.20-2.31 (m, 4H), 4.12-4.23 (m, 1H), 7.41 (t, J=7.78 Hz, 1H), 7.72 (d, J=7.93 Hz, 1H), 7.98 (d, J=7.63 Hz, 1H); Anal. Calcd for C$_{15}$H$_{18}$N$_4$O.1.6 TFA: C, 48.13; H, 4.48; N, 12.20. Found: C, 47.74; H, 4.54; N, 12.52.

EXAMPLE 16

2-{1-[(3,5-dimethylbenzyl)amino]cyclopropyl}-1H-benzimidazole-4-carboxamide

The title compound was prepared according to the procedure for Example 2, substituting Example 13 for Example 1C and 3,5-dimethylbenzaldehyde for propionaldehyde (15 mg, 13%). MS (DCI/NH$_3$), m/z 335 (M+H)$^+$; $^1$H NMR (400 MHz, DMSO-d6): δ 1.60-1.81 (m, 4H), 2.28 (s, 6H), 4.20-4.39 (m, 2H), 7.01 (s, 1H), 7.08 (s, 2H), 7.35 (t, J=7.83 Hz, 1H), 7.70 (d, J=7.98 Hz, 1H), 7.87 (d, J=7.67 Hz, 2H), 9.01 (s, 1H), 9.62 (s, 1H); Anal. Calcd for C$_{20}$H$_{22}$N$_4$O.1.2 TFA: C, 57.09; H, 4.96; N, 11.89. Found: C, 56.88; H, 5.08; N, 11.80.

EXAMPLE 17

2-{1-[(pyridin-4-ylmethyl)amino]cyclopropyl}-1H-benzimidazole-4-carboxamide

The title compound was prepared according to the procedure for Example 2, substituting Example 13 for Example 1C and 4-pyridine carboxaldehyde for propionaldehyde (62 mg, 58%). MS (DCI/NH$_3$), m/z 308 (M+H)$^+$; $^1$H NMR (400 MHz, CD$_3$OD): δ 1.61 (dd, J=8.75, 2.30 Hz, 4H), 4.31 (s, 2H), 7.51 (t, J=7.98 Hz, 1H), 7.82 (d, J=8.29 Hz, 1H), 7.97 (d, J=7.67 Hz, 1H), 8.06 (d, J=6.75 Hz, 2H), 8.72 (d, J=6.75 Hz, 2H); Anal. Calcd for C$_{17}$H$_{17}$N$_5$O.2.6 TFA: C, 43.99; H, 3.51; N, 11.30. Found: C, 43.64; H, 3.57; N, 11.43.

EXAMPLE 18

2-[1-(dipropylamino)cyclopropyl]-1H-benzimidazole-4-carboxamide

The title compound was prepared according to the procedure for Example 2, substituting Example 13 for Example 1C (45 mg, 43%). MS (DCI/NH$_3$), m/z 301 (M+H)$^+$; $^1$H NMR (500 MHz, CD$_3$OD): δ 1.00 (t, J=7.32 Hz, 6H), 1.67-1.76 (m, 4H), 1.83-1.87 (m, 4H), 3.23-3.28 (m, 4H), 7.46 (t, J=7.93 Hz, 1H), 7.78 (d, J=7.63 Hz, 1H), 8.00 (d, J=7.02 Hz, 1H); Anal. Calcd for C$_{17}$H$_{24}$N$_4$O.1.0 TFA: C, 55.00; H, 6.11; N, 13.47. Found: C, 54.60; H, 5.72; N, 13.22.

EXAMPLE 19

2-{1-[bis(cyclopropylmethyl)amino]cyclopropyl}-1H-benzimidazole-4-carboxamide

The title compound was prepared according to the procedure for Example 2, substituting Example 13 for Example 1C and cyclopropanecarboxaldehyde for propionaldehyde (66 mg, 59%). MS (DCI/NH$_3$), m/z 325 (M+H)$^+$; $^1$H NMR (500 MHz, CD$_3$OD): δ 0.45 (d, J=4.88 Hz, 4H), 0.78 (d, J=7.93 Hz, 4H), 1.28-1.41 (m, 2H), 1.79-1.89 (m, 2H), 1.95-2.03 (m, 2H), 3.33-3.89 (m, 4H), 7.45 (t, J=7.78 Hz, 1H), 7.78 (d, J=8.24 Hz, 1H), 8.00 (d, J=7.63 Hz, 1H); Anal. Calcd for C$_{19}$H$_{24}$N$_4$O.1.6 TFA: C, 52.61; H, 5.09; N, 11.05. Found: C, 52.80; H, 4.88; N, 11.15.

EXAMPLE 20

2-(1-aminocyclobutyl)-1H-benzimidazole-4-carboxamide

The title compound was prepared according to the procedures described in Examples 1A and 1B substituting 1-aminocyclobutanecarboxylic acid for 2-{[(benzyloxy)carbonyl]amino}-2-methylpropanoic acid (294 mg, 47%). MS (DCI/NH$_3$), m/z 231 (M+H)$^+$; $^1$H NMR (300 MHz, DMSO-d6): δ 1.98-2.21 (m, 2H), 2.33-2.47 (m, 2H), 2.65-2.72 (m, 2H), 6.73 (br s, 2H), 7.32 (t, J=7.80 Hz, 1H), 7.71 (d, J=8.14 Hz, 1H), 7.74 (s, 1H), 7.84 (d, J=7.46 Hz, 1H), 7.95 (s, 1H).

EXAMPLE 21

2-[1-(propylamino)cyclobutyl]-1H-benzimidazole-4-carboxamide

The title compound was prepared according to the procedure for Example 2, substituting Example 20 for Example 1C (16 mg, 18%). MS (DCI/NH$_3$), m/z 273 (M+H)$^+$; $^1$H NMR (500 MHz, CD$_3$OD): δ 1.00 (t, J=7.49 Hz, 3H), 1.69-1.80 (m, 2H), 2.21-2.32 (m, 2H), 2.83-2.88 (m, 4H), 2.89-2.93 (m, 2H), 7.45 (t, J=7.96 Hz, 1H), 7.82 (d, J=8.11 Hz, 1H), 8.02 (d, J=7.49 Hz, 1H); Anal. Calcd for C$_{15}$H$_{20}$N$_4$O.1.4 TFA: C, 49.49; H, 4.99; N, 12.97. Found: C, 49.34; H, 4.99; N, 12.96.

EXAMPLE 22

2-{1-[(cyclopropylmethyl)amino]cyclobutyl}-1H-benzimidazole-4-carboxamide

The title compound was prepared according to the procedure for Example 2, substituting Example 20 for Example 1C and cyclopropanecarboxaldehyde for propionaldehyde (43 mg, 46%). MS (DCI/NH$_3$), m/z 285 (M+H)$^+$; $^1$H NMR (500 MHz, CD$_3$OD): δ 0.32-0.39 (m, 2H), 0.68-0.75 (m, 2H), 1.04-1.15 (m, 1H), 2.23-2.33 (m, 2H), 2.81-2.89 (m, 6H), 7.45 (t, J=7.96 Hz, 1H), 7.81 (d, J=8.11 Hz, 1H), 8.02 (d, J=7.80 Hz, 1H); Anal. Calcd for C$_{16}$H$_{20}$N$_4$O.1.4 TFA: C, 50.86; H, 4.86; N, 12.62. Found: C, 51.21; H, 4.62; N, 12.62.

EXAMPLE 23

2-[1-(isopropylamino)cyclobutyl]-1H-benzimidazole-4-carboxamide

The title compound was prepared according to the procedure for Example 2, substituting Example 20 for Example 1C and acetone for propionaldehyde (16 mg, 18%). MS (DCI/NH$_3$), m/z 273 (M+H)$^+$; $^1$H NMR (500 MHz, CD$_3$OD): δ 1.25 (d, J=6.55 Hz, 6H), 2.08-2.28 (m, 2H), 2.84-2.99 (m, 4H), 3.15-3.27 (m, 1H), 7.47 (t, J=7.95 Hz, 1H), 7.85 (d, J=8.11 Hz, 1H), 8.03 (d, J=6.55 Hz, 1H).

EXAMPLE 24

2-[1-(dipropylamino)cyclobutyl]-1H-benzimidazole-4-carboxamide

The title compound was prepared according to the procedure for Example 2, substituting Example 20 for Example 1C. MS (DCI/NH$_3$), m/z 315 (M+H)$^+$; $^1$H NMR (500 MHz, CD$_3$OD): δ 0.99 (t, J=7.33 Hz, 6H), 1.70-1.90 (m, 5H), 2.01-2.13 (m, 1H), 2.87-2.99 (m, 3H), 3.05-3.21 (m, 5H), 7.50 (t, J=7.80 Hz, 1H), 7.86 (d, J=8.11 Hz, 1H), 8.06 (d, J=7.49 Hz, 1H).

EXAMPLE 25

2-[1-(dibutylamino)cyclobutyl]-1H-benzimidazole-4-carboxamide

The title compound was prepared according to the procedure for Example 2, substituting Example 20 for Example 1C and butyraldehyde for propionaldehyde (25 mg, 22%). MS (DCI/NH$_3$), m/z 343 (M+H)$^+$; $^1$H NMR (300 MHz, CD$_3$OD): δ 0.97 (t, J=7.29 Hz, 6H), 1.31-1.48 (m, 4H), 1.62-1.91 (m, 5H), 1.99-2.18 (m, 1H), 2.82-2.99 (m, 3H), 3.02-3.21 (m, 5H), 7.51 (t, J=7.80 Hz, 1H), 7.86 (d, J=8.14 Hz, 1H), 8.07 (d, J=7.46 Hz, 1H); Anal. Calcd for C$_{20}$H$_{30}$N$_4$O.1.7 TFA: C, 52.40; H, 5.96; N, 10.45. Found: C, 52.78; H, 5.57; N, 10.58.

EXAMPLE 26

2-(3-amino-1-methylpropyl)-1H-benzimidazole-4-carboxamide

EXAMPLE 26A dibenzyl azetidine-1,2-dicarboxylate

Benzyl azetidine-2-carboxylate (4.0 g, 21 mmol) and potassium carbonate (5 g, 36 mmol) in a mixture of 1,4-dioxane (25 ml) and water (30 ml) was treated with benzyl chloroformate (3 ml, 21 mmol) at room temperature for 6 hours. Piperazine (5 drops) was added and the mixture was stirred for additional 0.5 hour. The organic volatiles were removed in vacuo and the residue was partitioned between ethyl acetate and 2 N HCl solution. The upper layer was washed with brine and dried over MgSO$_4$. Removal of solvents afforded the desired compound (6.8 g, Yield: 96%). MS (DCI/NH$_3$) m/z 278 (M+H)$^+$.

EXAMPLE 26B dibenzyl 2-methylazetidine-1,2-dicarboxylate

Example 26A (325 mg, 1 mmol) and iodomethane (0.12 ml, 2.0 mmol) in THF (5 mL) was treated with NaN(TMS)$_2$ in THF (1.0 M, 2 mL, 2.0 mmol) at −70° C. under nitrogen. The temperature of the cooling bath was slowly raised to −20° C. within 1 h and the mixture was stirred at the same temperature for additional 2 h. After quenching with water, the mixture was partitioned between water and EtOAc. The organic phase was washed with water and concentrated. The residue was purified on flash column chromatograph to give Example 26B. (250 mg, 77% yield). MS (DCI/NH$_3$) m/z 340 (M+H)$^+$.

EXAMPLE 26C

1-[(benzyloxy)carbonyl]-2-methylazetidine-2-carboxylic acid

Example 26B (339 mg, 1.0 mmol) in a mixture of THF (5 mL) and water (3 mL) was treated with LiOH.H$_2$O (84 mg, 2.0 mmol) in water (3 mL). Methanol was added until a transparent solution formed (1 mL). This solution was heated at 60° C. for overnight and the organic solvents were removed under vacuum. The residual aqueous solution was acidified with 2 N HCl to pH 2 and was partitioned between ethyl acetate and water. The organic phase was washed with water, dried (MgSO$_4$), filtered and concentrated to give Example 26C (310 mg, 88% yield). MS (DCI/NH$_3$) m/z 250 (M+H)$^+$.

EXAMPLE 26D benzyl 2-({[2-amino-3-(aminocarbonyl)phenyl]amino}carbonyl)-2-methylazetidine-1-carboxylate Example 26C (1.67 g, 6.55 mmol) in a mixture of pyridine (15 mL) and DMF (15 mL) was treated with 1,1'-carbonyldiimidazole (1.27 g, 7.86 mmol) at 45° C. for 2 h. 2,3-Diaminobenzamide dihydrochloride (1.47 g, 6.55 mmol) was added and the mixture was stirred at rt overnight. After concentration, the residue was partitioned between ethyl acetate and diluted sodium bicarbonate aqueous solution. The formed slightly yellow solid material was collected by filtration, washed with water and ethyl acetate, and dried to give Example 26D (1.88 g). Yield: 75%. MS (APCI) m/z 383 (M+H)$^+$.

EXAMPLE 26E benzyl 2-[4-(aminocarbonyl)-1H-benzimidazol-2-yl]-2-methylazetidine-1-carboxylate Example 26D (1.88 g, 4.9 mmol) in acetic acid (50 mL) was heated under reflux for 2 h. After cooled, the solution was concentrated and the residual oil was partitioned between ethyl acetate and sodium bicarbonate aqueous solution. The organic phase was washed with water and concentrated. The residue was purified by flash column chromatography to provide Example 26E (350 mg, Yield: 22%). MS (APCI) m/z 365 (M+H)$^+$.

EXAMPLE 26F 2-(3-amino-1-methylpropyl)-1H-benzimidazole-4-carboxamide

Example 26E (0.35 g, 1.0 mmol) in methanol (5 ml) was treated with 10% Pd/C (8 mg) under hydrogen for overnight. Solid material was filtered off and the filtrate was concentrated. The residue was purified by HPLC (Zorbax, C-18, $CH_3CN/H_2O/CF_3CO_2H$) to afford Example 26 (Yield: 10%). MS (DCI/NH$_3$) m/z 233 (M+H)$^+$. $^1$H NMR (500 MHz, CD$_3$OD): δ 1.58 (d, J=7.06 Hz, 3H), 2.12-2.23 (m, 1H), 2.23-2.37 (m, 1H), 2.88-3.01 (m, 1H), 3.02-3.15 (m, 1H), 3.51-3.64 (m, 1H), 7.58 (t, 1H), 7.90 (d, J=7.36 Hz, 1H), 8.00 (d, J=7.67 Hz, 1H).

EXAMPLE 27

2-[3-(cyclopentylamino)-1-methylpropyl]-1H-benzimidazole-4-carboxamide

Example 26F (70 mg, 0.3 mmol) in methanol (5 mL) was treated with cyclopentanone (50 mg, 0.6 mmol) and stirred at room temperature for 1 hour. Triacetoxyborohydride (254 mg, 1.2 mmol) was added. After additional 3 h stirring, the reaction mixture was concentrated and the title compound was purified by HPLC (Zorbax, C-18, $CH_3CN/H_2O/CF_3CO_2H$) to give Example 27 (10 mg, Yield: 11%). MS (APCI) m/z 301 (M+H)$^+$; $^1$H NMR (500 MHz, CD$_3$OD): δ 1.58 (d, J=7.18 Hz, 3H), 1.59-1.71 (m, 3H), 1.74-1.85 (m, 3H), 2.03-2.14 (m, 2H), 2.15-2.26 (m, 1H), 2.27-2.38 (m, 1H), 2.97-3.07 (m, 1H), 3.11-3.21 (m, 1H), 3.49-3.61 (m, 2H), 7.56 (d, 1H), 7.89 (d, J=7.18 Hz, 1H), 7.99 (d, J=6.86 Hz, 1H).

EXAMPLE 28

2-[3-(cyclohexylamino)-1-methylpropyl]-1H-benzimidazole-4-carboxamide

The title compound was prepared according to the procedure for Example 27, substituting cyclohexanone for cyclopentanone. MS (APCI) m/z 315 (M+H)$^+$; $^1$H NMR (500 MHz, CD$_3$OD): δ 1.15-1.27 (m, 1H), 1.26-1.40 (m, 4H), 1.59 (d, J=7.18 Hz, 3H), 1.69 (d, J=12.79 Hz, 1H), 1.80-1.92 (m, 2H), 2.07 (d, J=4.99 Hz, 2H), 2.17-2.26 (m, 1H), 2.27-2.39 (m, 1H), 2.99-3.09 (m, 2H), 3.14-3.23 (m, 1H), 3.55-3.65 (m, 1H), 7.58 (d, 1H), 7.91 (d, J=7.49 Hz, 1H), 8.00 (d, J=7.49 Hz, 1H).

EXAMPLE 29

2-(1-aminoethyl)-1H-benzimidazole-4-carboxamide

The title compound was prepared according to the procedures for Example 1A-1C substituting 2-{[(benzyloxy)carbonyl]amino}propanoic acid for 2-{[(benzyloxy)carbonyl]amino}-2-methylpropanoic acid in Example 1A (830 mg, 92%). MS (DCI/NH$_3$), m/z 205 (M+H)$^+$; $^1$H NMR (300 MHz, DMSO-d6): δ 1.46 (d, J=6.78 Hz, 3H), 4.25 (q, J=6.78 Hz, 1H), 7.24 (t, J=7.63 Hz, 1H), 7.65 (d, J=7.80 Hz, 1H), 7.69 (s, 1H), 7.78 (d, J=7.12 Hz, 1H), 9.33 (s, 1H).

EXAMPLE 30

2-[1-(propylamino)ethyl]-1H-benzimidazole-4-carboxamide

The title compound was prepared according to the procedure for Example 2, substituting Example 29 for Example 1C (24 mg, 7%). MS (DCI/NH$_3$), m/z 247 (M+H)$^+$; $^1$H NMR (400 MHz, CD$_3$OD): δ 1.04 (t, J=7.36 Hz, 3H), 1.76-1.80 (m, 2H), 1.82 (d, J=7.06 Hz, 3H), 3.02-3.20 (m, 2H), 4.82-4.87 (m, 1H), 7.42 (t, J=7.83 Hz, 1H), 7.79 (d, J=8.29 Hz, 1H), 7.98 (d, J=7.36 Hz, 1H).

EXAMPLE 31

2-[1-(butylamino)ethyl]-1H-benzimidazole-4-carboxamide

The title compound was prepared according to the procedure for Example 2, substituting Example 29 for Example 1C and butyraldehyde for propionaldehyde (15 mg, 16%). MS (DCI/NH$_3$), m/z 261 (M+H)$^+$; $^1$H NMR (400 MHz, CD$_3$OD): δ 0.98 (t, J=7.36 Hz, 3H), 1.38-1.52 (m, 2H), 1.68-1.79 (m, 2H), 1.82 (d, J=6.75 Hz, 3H), 3.03-3.23 (m, 2H), 4.83-4.88 (m, 1H), 7.42 (t, J=7.82 Hz, 1H), 7.79 (d, J=7.98 Hz, 1H), 7.98 (d, J=7.67 Hz, 1H).

EXAMPLE 32

2-{1-[(cyclopropylmethyl)amino]ethyl}-1H-benzimidazole-4-carboxamide

The title compound was prepared according to the procedure for Example 2, substituting Example 29 for Example 1C and cyclopropanecarboxaldehyde for propionaldehyde (29 mg, 31%). MS (DCI/NH$_3$), m/z 259 (M+H)$^+$; $^1$H NMR (500 MHz, CD$_3$OD): δ 0.34-0.47 (m, 2H), 0.67-0.83 (m, 2H), 1.07-1.24 (m, 1H), 1.82 (d, J=6.86 Hz, 3H), 2.99 (dd, J=12.95, 7.64 Hz, 1H), 3.05-3.15 (m, 1H), 4.86 (q, J=6.86 Hz, 1H), 7.42 (t, J=7.80 Hz, 1H), 7.79 (d, J=8.11 Hz, 1H), 7.98 (d, J=7.49 Hz, 1H); Anal. Calcd for $C_{14}H_{18}N_4O$.3.0HCl: C, 45.73; H, 5.76; N, 15.24. Found: C, 45.52; H, 6.15; N, 15.04.

EXAMPLE 33

2-[1-(isobutylamino)ethyl]-1H-benzimidazole-4-carboxamide

The title compound was prepared according to the procedure for Example 2, substituting Example 29 for Example 1C and isobutyraldehyde for propionaldehyde (60 mg, 63%). MS (DCI/NH$_3$), m/z 261 (M+H)$^+$; $^1$H NMR (400 MHz, CD$_3$OD): δ 1.07 (dd, J=6.60, 4.45 Hz, 6H), 1.84 (d, J=6.75 Hz, 3H), 1.98-2.18 (m, 1H), 2.91-2.98 (m, 1H), 2.99-3.08 (m, 1H), 4.83-4.89 (m, 1H), 7.42 (t, J=7.83 Hz, 1H), 7.79 (d, J=7.06 Hz, 1H), 7.98 (d, J=7.67 Hz, 1H); Anal. Calcd for $C_{14}H_{20}N_4O.1.4$ TFA: C, 48.05; H, 5.14; N, 13.34. Found: C, 47.77; H, 5.01; N, 13.41.

EXAMPLE 34

2-[1-(isopropylamino)ethyl]-1H-benzimidazole-4-carboxamide

The title compound was prepared according to the procedure for Example 2, substituting Example 29 for Example 1C and acetone for propionaldehyde (90 mg, 99%). MS (DCI/$NH_3$), m/z 247 (M+H)$^+$; $^1$H NMR (400 MHz, $CD_3OD$): δ 1.40 (dd, J=6.44, 4.60 Hz, 6H), 1.81 (d, J=6.75 Hz, 3H), 3.46-3.59 (m, 1H), 4.93 (q, J=7.06 Hz, 1H), 7.42 (t, J=7.83 Hz, 1H), 7.80 (d, J=8.29 Hz, 1H), 7.98 (d, J=7.67 Hz, 1H); Anal. Calcd for $C_{13}H_{18}N_4O.1.5$ TFA: C, 46.05; H, 4.71; N, 13.42. Found: C, 46.08; H, 4.76; N, 13.74.

EXAMPLE 35

2-[1-(cyclopentylamino)ethyl]-1H-benzimidazole-4-carboxamide

The title compound was prepared according to the procedure for Example 2, substituting Example 29 for Example 1C and cyclopentanone for propionaldehyde (63 mg, 63%). MS (DCI/$NH_3$), m/z 273 (M+H)$^+$; $^1$H NMR (400 MHz, $CD_3OD$): δ 1.60-1.79 (m, 4H), 1.79-1.87 (m, J=5.00 Hz, 2H), 1.83 (d, J=6.75 Hz, 3H), 2.01-2.13 (m, 1H), 2.14-2.25 (m, 1H), 3.60-3.75 (m, 1H), 4.83-4.90 (m, 1H), 7.42 (t, J=7.83 Hz, 1H), 7.80 (d, J=8.29 Hz, 1H), 7.98 (d, J=7.67 Hz, 1H); Anal. Calcd for $C_{15}H_{20}N_4O.1.5$ TFA: C, 48.76; H, 4.89; N, 12.64. Found: C, 49.06; H, 4.99; N, 13.03.

EXAMPLE 36

2-[1-(cyclohexylamino)ethyl]-1H-benzimidazole-4-carboxamide

The title compound was prepared according to the procedure for Example 2, substituting Example 29 for Example 1C and cyclohexanone for propionaldehyde (85 mg, 81%). MS (DCI/$NH_3$), m/z 287 (M+H)$^+$; $^1$H NMR (400 MHz, $CD_3OD$): δ 1.15-1.37 (m, 3H), 1.38-1.52 (m, 2H), 1.70 (d, J=12.58 Hz, 2H), 1.81 (d, J=6.75 Hz, 3H), 1.88 (dd, J=12.58, 2.45 Hz, 2H), 2.09-2.18 (m, 1H), 2.18-2.29 (m, 1H), 3.14-3.27 (m, 1H), 7.42 (t, J=7.83 Hz, 1H), 7.80 (d, J=7.98 Hz, 1H), 7.98 (d, J=7.06 Hz, 1H); Anal. Calcd for $C_{16}H_{22}N_4O.1.4$ TFA: C, 50.63; H, 5.29; N, 12.56. Found: C, 50.34; H, 5.22; N, 12.57.

EXAMPLE 37

2-{1-[(2-phenylethyl)amino]ethyl}-1H-benzimidazole-4-carboxamide

The title compound was prepared according to the procedure for Example 2, substituting Example 29 for Example 1C and phenylacetaldehyde for propionaldehyde (28 mg, 25%). MS (DCI/$NH_3$), m/z 309 (M+H)$^+$; $^1$H NMR (400 MHz, $CD_3OD$): δ 1.83 (d, J=7.06 Hz, 3H), 3.07 (t, J=8.13 Hz, 2H), 3.33-3.49 (m, 2H), 4.87 (q, J=6.75 Hz, 1H), 7.24-7.29 (m, 3H), 7.30-7.36 (m, 2H), 7.42 (t, J=7.82 Hz, 1H), 7.79 (d, J=8.29 Hz, 1H), 7.98 (d, J=7.36 Hz, 1H); Anal. Calcd for $C_{18}H_{20}N_4O.1.4$ TFA: C, 53.38; H, 4.61; N, 11.97. Found: C, 53.46; H, 4.69; N, 12.09.

EXAMPLE 38

2-[1-(dipropylamino)ethyl]-1H-benzimidazole-4-carboxamide

The title compound was prepared according to the procedure for Example 2, substituting Example 29 for Example 1C (40 mg, 38%). MS (DCI/$NH_3$), m/z 289 (M+H)$^+$; $^1$H NMR (400 MHz, $CD_3OD$): δ 1.01 (t, J=7.36 Hz, 6H), 1.77-1.87 (m, 4H), 1.89 (d, J=7.06 Hz, 3H), 3.21-3.30 (m, 4H), 5.11 (q, J=6.85 Hz, 1H), 7.44 (t, J=7.82 Hz, 1H), 7.82 (d, J=7.36 Hz, 1H), 8.00 (d, J=7.67 Hz, 1H); Anal. Calcd for $C_{16}H_{24}N_4O.2.6HCl$: C, 50.15; H, 7.00; N, 14.62. Found: C, 50.08; H, 7.39; N, 14.50.

EXAMPLE 39

2-{1-[butyl(pentyl)amino]ethyl}-1H-benzimidazole-4-carboxamide

The title compound was prepared according to the procedure for Example 2, substituting Example 29 for Example 1C and butyraldehyde for propionaldehyde (30 mg, 26%). MS (DCI/$NH_3$), m/z 317 (M+H)$^+$; $^1$H NMR (400 MHz, $CD_3OD$): δ 0.97 (t, J=7.36 Hz, 6H), 1.35-1.48 (m, 4H), 1.71-1.83 (m, 4H), 1.89 (d, J=7.06 Hz, 3H), 3.25-3.37 (m, 4H), 5.12 (q, J=6.85 Hz, 1H), 7.45 (t, J=7.83 Hz, 1H), 7.83 (d, J=7.98 Hz, 1H), 8.00 (d, J=7.36 Hz, 1H); Anal. Calcd for $C_{18}H_{28}N_4O.2.2HCl$: C, 54.50; H, 7.67; N, 14.12. Found: C, 54.68; H, 7.76; N, 13.93.

EXAMPLE 40

2-{1-[bis(cyclopropylmethyl)amino]ethyl}-1H-benzimidazole-4-carboxamide

The title compound was prepared according to the procedure for Example 2, substituting Example 29 for Example 1C and cyclopropanecarboxaldehyde for propionaldehyde (31 mg, 27%). MS (DCI/$NH_3$), m/z 313 (M+H)$^+$; $^1$H NMR (400 MHz, $CD_3OD$): δ 0.38-0.56 (m, 4H), 0.73-0.89 (m, 4H), 1.16-1.31 (m, 2H), 1.88 (d, J=6.75 Hz, 3H), 3.25 (dd, J=13.50, 7.36 Hz, 2H), 3.50 (dd, J=13.50, 6.75 Hz, 2H), 5.40 (q, J=7.06 Hz, 1H), 7.44 (t, J=7.82 Hz, 1H), 7.82 (d, J=7.98 Hz, 1H), 7.99 (d, J=7.67 Hz, 1H); Anal. Calcd for $C_{18}H_{24}N_4O.2.6HCl$: C, 53.09; H, 6.58; N, 13.76. Found: C, 53.25; H, 6.80; N, 13.61.

EXAMPLE 41

2-(1-{[(dimethylamino)sulfonyl]amino}ethyl)-1H-benzimidazole-4-carboxamide

The title compound was prepared according to the procedure for Example 11 substituting Example 29 for Example 1C (35 mg, 31%). MS (DCI/$NH_3$), m/z 312 (M+H)$^+$; $^1$H NMR (400 MHz, $CD_3OD$): δ 1.72 (d, J=7.36 Hz, 3H), 2.76 (s, 6H), 5.03 (q, J=7.06 Hz, 1H), 7.57 (t, J=7.98 Hz, 1H), 7.89 (d, J=8.29 Hz, 1H), 8.01 (d, J=7.67 Hz, 1H); Anal. Calcd for $C_{12}H_{17}N_5O_3S.1.4$ TFA: C, 37.74; H, 3.94; N, 14.87. Found: C, 37.78; H, 3.79; N, 15.02.

EXAMPLE 42

2-(1-aminopropyl)-1H-benzimidazole-4-carboxamide

Example 42 was obtained as a side product from the reaction of Example 13 (14 mg, 2%). MS (DCI/$NH_3$), m/z 219

(M+H)+; 1H NMR (400 MHz, CD3OD): δ 1.04 (t, J=7.52 Hz, 3H), 2.09-2.31 (m, 2H), 4.68 (t, J=6.75 Hz, 1H), 7.41 (t, J=7.98 Hz, 1H), 7.77 (d, J=7.98 Hz, 1H), 7.98 (d, J=7.67 Hz, 1H).

EXAMPLE 43

2-[(1R)-1-(dimethylamino)-2-phenylethyl]-1H-benzimidazole-4-carboxamide

The title compound was prepared according to the procedures for Example 1A-1C substituting N,N-dimethyl-L-phenylalanine for 2-{[(benzyloxy)carbonyl]amino}-2-methylpropanoic acid in Example 1A (110 mg, 7%). MS (DCI/NH3), m/z 309 (M+H)+; 1H NMR (400 MHz, CD3OD): δ 3.09 (s, 6H), 3.68-3.79 (m, 2H), 5.16 (dd, J=10.13, 5.83 Hz, 1H), 7.11-7.22 (m, 5H), 7.50 (t, J=7.82 Hz, 1H), 7.83 (d, J=8.29 Hz, 1H), 8.02 (d, J=7.06 Hz, 1H).

EXAMPLE 44

2-[1-(piperidin-4-yloxy)ethyl]-1H-benzimidazole-4-carboxamide

EXAMPLE 44A benzyl 4-(2-tert-butoxy-1-methyl-2-oxoethoxy)piperidine-1-carboxylate Benzyl 4-hydroxypiperidine-1-carboxylate (11.8 g, 50.2 mmol) in DMF (100 mL) was treated with NaH (2.6 g, 65.2 mmol) at room temperature for 1 hr. tert-Butyl 2-bromopropanoate (15.7 g, 75.3 mmol) was added and the solution was heated at 110° C. for 16 hrs. After cooled, the reaction mixture was partitioned between water and ethyl acetate. The organic phase was concentrated and the residue was purified by flash column chromatography (silica gel, 5%-100% EtOAc/hexanes) to give Example 44A (6.7 g, 37%). MS (DCI/NH3), m/z 364 (M+H)+.

EXAMPLE 44B 2-({1-[(benzyloxy)carbonyl]piperidin-4-yl}oxy)propanoic acid

Example 44A (6.7 g) in TFA (50 mL) was stirred at 0° C. for 0.5 h and at room temperature for 4 h. The reaction mixture was concentrated and dried to provide crude Example 44B. This material was used for the next step without further purification. MS (DCI/NH3), m/z 308 (M+H)+.

EXAMPLE 44C benzyl 4-(2-{[2-amino-3-(aminocarbonyl)phenyl]amino}-1-methyl-2-oxoethoxy)piperidine-1-carboxylate The title compound was prepared according to the procedure for Example 1A substituting Example 44B for 2-{[(benzyloxy)carbonyl]amino}-2-methylpropanoic acid. MS (DCI/NH3), m/z 441 (M+H)+.

EXAMPLE 44D benzyl 4-{1-[4-(aminocarbonyl)-1H-benzimidazol-2-yl]ethoxy}piperidine-1-carboxylate The title compound was prepared according to the procedure for Example 1B substituting Example 44C for Example 1A. MS (DCI/NH3), m/z 423 (M+H)+

EXAMPLE 44E

2-[1-(piperidin-4-yloxy)ethyl]-1H-benzimidazole-4-carboxamide

The title compound was prepared according to the procedure for Example 1C substituting Example 44D for Example 1B (269 mg, 79%). MS (DCI/NH3), m/z 289 (M+H)+; 1H NMR (300 MHz, DMSO-d6): δ 1.55 (d, J=6.44 Hz, 3H), 1.59-1.68 (m, 1H), 1.75-1.88 (m, 1H), 1.94-2.09 (m, 1H), 2.67-2.85 (m, 2H), 2.99-3.17 (m, 3H), 3.55-3.70 (m, 1H), 4.99 (q, J=6.44 Hz, 1H), 7.31 (t, J=7.80 Hz, 1H), 7.69 (d, J=8.14 Hz, 1H), 7.70 (s, 1H), 7.82 (d, J=7.12 Hz, 1H), 9.20 (s, 1H), 12.87 (s, 1H).

EXAMPLE 45

2-{1-[(1-isopropylpiperidin-4-yl)oxy]ethyl}-1H-benzimidazole-4-carboxamide

The title compound was prepared according to the procedure for Example 2, substituting Example 44E for Example 1C and substituting acetone for propionaldehyde (49 mg, 61%). MS (DCI/NH3), m/z 331 (M+H)+; 1H NMR (500 MHz, CD3OD): δ 1.35 (d, J=6.71 Hz, 3H), 1.41 (d, J=6.71 Hz, 3H), 1.72 (d, J=6.71 Hz, 2H), 1.76 (d, J=6.71 Hz, 2H), 1.87-2.02 (m, 1H), 2.02-2.14 (m, 1H), 2.22 (dd, J=31.58, 12.97 Hz, 1H), 2.29-2.49 (m, 1H), 3.01-3.14 (m, 1H), 3.33-3.36 (m, 1H), 3.37-3.42 (m, 1H), 3.43-3.50 (m, 1H), 3.52-3.58 (m, 1H), 5.23-5.58 (m, 1H), 7.68-7.73 (m, 1H), 8.02 (dd, J=16.48, 8.24 Hz, 1H), 8.08 (dd, J=7.63, 2.14 Hz, 1H).

EXAMPLE 46

2-{1-[(1-cyclobutylpiperidin-4-yl)oxy]ethyl}-1H-benzimidazole-4-carboxamide

The title compound was prepared according to the procedure for Example 2, substituting Example 44E for Example 1C and substituting cyclobutanone for propionaldehyde (17 mg, 21%). MS (DCI/NH3), m/z 343 (M+H)+; 1H NMR (500 MHz, CD3OD): δ 1.72 (d, J=6.71 Hz, 2H), 1.75 (d, J=6.71 Hz, 2H), 1.80-1.94 (m, 3H), 1.98-2.07 (m, 1H), 2.22-2.36 (m, 5H), 2.36-2.46 (m, 1H), 2.76-2.90 (m, 1H), 3.06-3.24 (m, 1H), 3.33-3.50 (m, 1H), 3.51-3.68 (m, 1H), 3.72-3.89 (m, 1H), 5.19-5.82 (m, 1H), 7.67-7.73 (m, 1H), 8.01 (dd, J=18.00, 8.24 Hz, 1H), 8.08 (d, J=7.63 Hz, 1H); Anal. Calcd for C19H26N4O2.3.5HCl: C, 48.55; H, 6.33; N, 11.92. Found: C, 48.36; H, 6.46; N, 11.91.

EXAMPLE 47

2-(1-amino-1-methylethyl)-5-chloro-1H-benzimidazole-7-carboxamide

EXAMPLE 47A 2-amino-5-chloro-3-nitrobenzamide

2-Amino-3-nitrobenzamide (4.0 g) in warm anhydrous acetonitrile (1.25 L) was treated with N-chlorosuccinimide (3.1 g) at 60° C. under nitrogen for 20 hours. The mixture was allowed to cool to room temperature and filtered. The filter cake was washed with acetonitrile and dried to provide the title compound (3.98 g, 84%). MS (DCI/NH$_3$) m/z 216 (M+H)$^+$.

EXAMPLE 47B 2,3-diamino-5-chlorobenzamide

Example 47A (2.9 g) in THF (300 mL) and ethanol (300 mL) was treated with Raney nickel (50% in water, 1.5 g) and stirred at room temperature under hydrogen (balloon) for 18 hours. The mixture was filtered and the filtrate was concentrated to provide the title compound (2.48 g, 99%). MS (DCI/NH$_3$) m/z 186 (M+H)$^+$.

EXAMPLE 47C benzyl 1-[4-(aminocarbonyl)-6-chloro-1H-benzimidazol-2-yl]-1-methylethylcarbamate 2-{[(Benzyloxy)carbonyl]amino}-2-methylpropanoic acid (320 mg) in a mixture of DMF (4 mL) and pyridine (4 mL) was treated with 1,1-carbonyldiimidazole (230 mg) at room temperature and stirred at 50° C. for 3 hours. The mixture was treated with Example 47B (250 mg) and stirred at 50° C. overnight. The mixture was allowed to cool to room temperature and was concentrated. The residue was treated with glacial acetic acid (20 mL) and heated at 110° C. for 2 hours, allowed to cool to room temperature and concentrated. The residue was purified by flash chromatography on silica gel to provide the title compound (21 mg, 4%). MS (DCI/NH$_3$) m/z 387 (M+H)$^+$.

EXAMPLE 47D 2-(1-amino-1-methylethyl)-5-chloro-1H-benzimidazole-7-carboxamide Example 47C (21 mg) in TFA (5 mL) was refluxed for 18 hours, allowed to cool to room temperature, and concentrated. The residue was purified on HPLC (Zorbax, C-18) to provide the title compound (8 mg, 59%). MS (DCI/NH$_3$) m/z 253 (M+H)$^+$; $^1$H NMR (500 MHz, CD$_3$OD) δ 1.87 (s, 6H), 7.76 (d, J=1.84 Hz, 1H), 7.93 (d, J=2.15 Hz, 1H).

EXAMPLE 48

2-(1-aminocyclohexyl)-1H-benzimidazole-4-carboxamide

EXAMPLE 48A

[1-(2-Amino-3-carbamoyl-phenylcarbamoyl)-cyclohexyl]-carbamic acid 9H-fluoren-9-ylmethyl ester A solution of 1-(9H-fluoren-9-ylmethoxycarbonyl amino)-cyclohexanecarboxylic acid (0.326 g, 0.9 mmol) in pyridine (1 mL) and DMF (1 ml) was heated to 40° C. for 30 min. Carbonyl diimidazole (0.15 g, 0.9 mmol) was added and the mixture was stirred at 40° C. for 1 hour then treated with 2,3-diamino-benzamide dihydrochloride (prepared as described in WO0026192, 0.2 g, 0.9 mmol). After stirring for 1 hour at room temperature, isopropyl alcohol (3 ml) was added and the solution was cooled overnight at 0° C. The precipitated solid was filtered, dissolved in water (3 ml), treated with 50% aqueous NaOH (0.071 ml) then stirred for 3 hours at room temperature. The mixture was filtered and used immediately in Example 48B.

EXAMPLE 48B 2-(1-aminocyclohexyl)-1H-benzimidazole-4-carboxamide

A solution of Example 48A in acetic acid (10 ml), was refluxed overnight then concentrated under vacuum. The residue was dissolved in water and treated with 50% aqueous NaOH (0.2 ml). The mixture was filtered and the mother liquor was concentrated and purified first by chromatoghraphy on silica gel, eluting with 10% MeOH/CH$_2$Cl$_2$/0.1% NH$_4$OH then by HPLC on a C18 column with 0-100% CH$_3$CN/H$_2$O/0.1% TFA to provide Example 48B as the trifluoroacetate salt. MS (ESI) m/e 281 (M+Na)$^+$. $^1$HNMR (DMSO-D6) δ ppm 8.63 (s, 2H), 7.88 (d, J=7.67 Hz, 1H), 7.78 (d, J=7.67 Hz, 2H), 7.37 (t, J=7.83 Hz, 1H), 2.42 (s, 2H), 1.96 (s, 2H), 1.73 (s, 2H), 1.54 (d, J=9.21 Hz, 4H).

EXAMPLE 49

9H-fluoren-9-ylmethyl 4-[4-(aminocarbonyl)-1H-benzimidazol-2-yl]piperidin-4-ylcarbamate

EXAMPLE 49A benzyl 4-[4-(aminocarbonyl)-1H-benzimidazol-2-yl]-4-{[(9H-fluoren-9-ylmethoxy)carbonyl]amino}piperidine-1-carboxylate The title compound was prepared as described for Example 48A and 48B by substituting 4-(9H-fluoren-9-ylmethoxycarbonylamino)-piperidine-1,4-dicarboxylic acid monobenzyl ester for 1-(9H-fluoren-9-ylmethoxycarbonyl amino)-cyclohexanecarboxylic acid. MS (ESI) m/e 616 (M+H)$^+$.

EXAMPLE 49B 9H-fluoren-9-ylmethyl 4-[4-(aminocarbonyl)-1H-benzimidazol-2-yl]piperidin-4-ylcarbamate A mixture of Example 49A (0.175 g, 0.3 mmol) and 10% Pd/C (0.015 g) in MeOH (5 ml) and acetic acid (0.2 ml), was stirred overnight under a H$_2$ atmosphere at room temperature. The mixture was filtered through a pad of silica then concentrated under vacuum. The residue was purified by HPLC on a C18 column with 0-100% CH$_3$CN/H$_2$O/0.1% TFA to provide 0.095 g (69%) of the desired product. MS (ESI) m/e 482 (M+H)$^+$. $^1$H NMR (DMSO-D6) δ ppm 8.55 (s, 1H), 8.42 (s, 1H), 8.15 (s, 1H), 7.82-7.91 (m, 3H), 7.65-7.78 (s, 3H) 7.42 (d, J=7.67 Hz 2H), 7.29-7.34 (m, 2H), 4.31 (d, J=7.06 Hz, 2H), 3.5-3.28 (m, 7H), 2.42 (s, 2H).

33

EXAMPLE 50 benzyl 4-amino-4-[4-(aminocarbonyl)-1H-benzimi-
dazol-2-yl]piperidine-1-carboxylate A mixture of Example 49A (0.035 g, 0.1 mmol) in DMF (2 ml) and piperidine (0.5 ml), was stirred at room temperature for 2 h. The mixture was concentrated under vacuum then crystallized from MeOH to provide 0.014 g (64%) of the desired product. MS (ESI) m/e 416 (M+Na)$^+$. $^1$H NMR (DMSO-D6) δ ppm 8.14 (s, 1H), 7.84 (d, J=7.02 Hz 1H), 7.73 (s, 2H) 7.37-7.40 (m, 4H), 7.31-7.37 (m, 2H), 5.11 (s, 2H), 3.51-3.68 (m, 6H), 2.32 (s, 2H), 1.88 (d, J=13.43 Hz, 2H).

EXAMPLE 51

[2-(4-Amino-piperidin-4-yl]-1H-benzoimidazole-4-
carboxylic acid amide

The title compound was prepared as described in Example 50 by substituting Example 49B for Example 49A. MS (DCI) m/e 260 (M+H)$^+$. $^1$H NMR (DMSO-D6) δ ppm 8.38 (s, 1H), 7.80 (d, J=7.32 Hz, 1H), 7.68 (d, J=7.93 Hz, 1H), 7.27 (t, J=7.63 Hz, 1H), 2.91-3.26 (m, 4H), 2.23-2.32 (m, 2H) 1.86 (d, J=13.73 Hz, 2H).

EXAMPLE 52

2-(2-amino-1,2,3,4-tetrahydronaphthalen-2-yl)-1H-
benzimidazole-4-carboxamide

The title compound was prepared as described in Examples 48A, 48B and 50, substituting 2-(9H-fluoren-9-ylmethoxy-carbonylamino)-1,2,3,4-napthalene-2-carboxylic acid for 1-(9H-fluoren-9-ylmethoxycarbonyl amino)-cyclohexan-ecarboxylic acid in Example 48A. MS (ESI) m/e 329 (M+Na)$^+$. $^1$H NMR (DMSO-D6) δ ppm 8.14 (s, 1H) 7.78 (d, J=7.32 Hz, 1H), 7.66 (d, J=7.93 Hz, 1H), 7.59 (s, 1H), 7.26 (s, 1H), 7.07-7.13 (m, 5H), 3.49 (d, J=16.48 Hz, 1H), 3.00-3.07 (m, 1H), 2.95 (d, J=16.78 Hz, 1H), 2.70-2.78 (m, 1H) 2.27-2.35 (m, 2H) 2.02-2.10 (m, 1H).

EXAMPLE 53

2-(2-amino-2,3-dihydro-1H-inden-2-yl)-1H-benz-
imidazole-4-carboxamide

The title compound was prepared as described in Examples 48A and 48B, substituting 2-(9H-fluoren-9-ylmethoxycarbo-nylamino)-indan-2-carboxylic acid for (9H-fluoren-9-yl-methoxycarbonyl amino)-cyclohexanecarboxylic acid in Example 48A. MS (ESI) m/e 315 (M+Na)$^+$. $^1$H NMR (DMSO-D6) δ ppm 7.79 (d, J=7.32 Hz, 1H), 7.68 (d, J=7.93 Hz, 1H), 7.59 (s, 1H), 7.23-7.29 (m, 4H), 7.17 (dd, J=5.34, 3.20 Hz, 2H), 5.75 (s, 1H), 3.66 (d, J=15.87 Hz, 3H), 3.11 (d, J=15.87 Hz, 3H).

34

What is claimed is:
1. A compound of Formula (I)

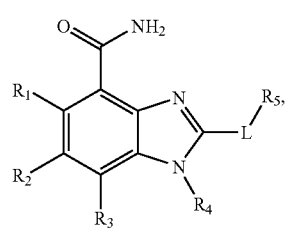

or a therapeutically acceptable salt thereof, wherein
$R_1$, $R_2$, and $R_3$ are independently selected from the group consisting of hydrogen, alkenyl, alkoxy, alkoxycarbo-nyl, alkyl, alkynyl, cyano, haloalkoxy, haloalkyl, halo-gen, hydroxy, hydroxyalkyl, nitro, $NR_AR_B$, and $(NR_AR_B)$carbonyl;
L is selected from the group consisting of straight or branched chain alkenylene, branched chain alkylene, and straight or branched chain alkynylene;
$R_4$ is selected from the group consisting of hydrogen, alkoxyalkyl, alkyl, heterocylealkyl, hydroxyalkyl, and $(NR_AR_B)$alkyl;
$R_5$ is $NR_CR_D$;
$R_A$ and $R_B$ are independently selected from the group consisting of hydrogen, alkyl, and alkycarbonyl;
$R_C$ and $R_D$ are independently selected from the group consisting of hydrogen, alkyl, alkycarbonyl, alkoxycarbo-nyl, alkoxycarbonylcycloalkyl, alkoxycarbonylaryl, arylalkyl, arylalkoxy, arylalkoxycarbonyl, cycloalkyl, cycloalkylalkyl, heteroaryl, heteroarylalkyl, hetero-cycle, heterocylealkyl, $(NR_ER_F)$alkyl, $(NR_ER_F)$carbo-nyl, and $(NR_ER_F)$sulfonyl; and
$R_E$ and $R_F$ are independently selected from the group consisting of hydrogen, alkyl, aryl, arylalkyl, cycloalkyl, cycloalkylalkyl, heteroaryl, heteroarylalkyl, hetero-cycle, and heterocylealkyl.
2. The compound according to claim 1 wherein L is a branched chain alkylene.
3. The compound according to claim 1 selected from the group consisting of
2-(1-amino-1-methylethyl)-1H-benzimidazole-4-car-boxamide;
2-[1-methyl-1-(propylamino)ethyl]-1H-benzimidazole-4-carboxamide;
2-[1-(butylamino)-1-methylethyl]-1H-benzimidazole-4-carboxamide;
2-{1-methyl-1-[(2-phenylethyl)amino]ethyl}-1H-benz-imidazole-4-carboxamide;
2-[1-(isopropylamino)-1-methylethyl]-1H-benzimida-zole-4-carboxamide;
2-{1-[(cyclopropylmethyl)amino]-1-methylethyl}-1H-benzimidazole-4-carboxamide;
2-[1-(cyclobutylamino)-1-methylethyl]-1H-benzimida-zole-4-carboxamide;
2-[1-(cyclopentylamino)-1-methylethyl]-1H-benzimida-zole-4-carboxamide;
2-(1-{[(cyclopentylamino)carbonyl]amino}-1-methyl-ethyl)-1H-benzimidazole-4-carboxamide;
2-(1-{[(ethylamino)carbonyl]amino}-1-methylethyl)-1H-benzimidazole-4-carboxamide;
2-(1-{[(dimethylamino)sulfonyl]amino}-1-methylethyl)-1H-benzimidazole-4-carboxamide;

2-(3-amino-1-methylpropyl)-1H-benzimidazole-4-carboxamide;
2-[3-(cyclopentylamino)-1-methylpropyl]-1H-benzimidazole-4-carboxamide;
2-[3-(cyclohexylamino)-1-methylpropyl]-1H-benzimidazole-4-carboxamide;
2-(1-aminoethyl)-1H-benzimidazole-4-carboxamide;
2-[1-(propylamino)ethyl]-1H-benzimidazole-4-carboxamide;
2-[1-(butylamino)ethyl]-1H-benzimidazole-4-carboxamide;
2-{1-[(cyclopropylmethyl)amino]ethyl}-1H-benzimidazole-4-carboxamide;
2-[1-(isobutylamino)ethyl]-1H-benzimidazole-4-carboxamide;
2-[1-(isopropylamino)ethyl]-1H-benzimidazole-4-carboxamide;
2-[1-(cyclopentylamino)ethyl]-1H-benzimidazole-4-carboxamide;
2-[1-(cyclohexylamino)ethyl]-1H-benzimidazole-4-carboxamide;
2-{1-[(2-phenylethyl)amino]ethyl}-1H-benzimidazole-4-carboxamide;
2-[1-(dipropylamino)ethyl]-1H-benzimidazole-4-carboxamide;
2-{1-[butyl(pentyl)amino]ethyl}-1H-benzimidazole-4-carboxamide;
2-{1-[bis(cyclopropylmethyl)amino]ethyl}-1H-benzimidazole-4-carboxamide;
2-(1-{[(dimethylamino)sulfonyl]amino}ethyl)-1H-benzimidazole-4-carboxamide;
2-(1-aminopropyl)-1H-benzimidazole-4-carboxamide;
2-[(1R)-1-(dimethylamino)-2-phenylethyl]-1H-benzimidazole-4-carboxamide; and
2-(1-amino-1-methylethyl)-5-chloro-1H-benzimidazole-7-carboxamide.

4. A pharmaceutical composition comprising a compound of Formula (I), according to claim 1, or a therapeutically acceptable salt thereof, in combination with a therapeutically acceptable carrier.

5. The compound according to claim 2, wherein the alkylene is —CH(CH$_3$)—, —C(CH$_3$)$_2$—, —CH(CH$_2$Ph)—, —CH(CH$_3$)CH$_2$CH(Ph)CH$_2$—, —CH$_2$CH(CH$_3$)CH$_2$—, or —CH(CH$_3$)CH$_2$CH$_2$—.

6. The compound according to claim 1, wherein R$_1$, R$_2$, and R$_3$ are independently selected from the group consisting of hydrogen, alkyl, and halogen, and wherein R$_4$ is hydrogen.

7. The compound according to claim 6, wherein R$_C$ and R$_D$ are independently selected from the group consisting of hydrogen, alkyl, alkycarbonyl, arylalkyl, cycloalkyl, cycloalkylalkyl, (NR$_E$R$_F$)carbonyl, and (NR$_E$R$_F$)sulfonyl; and R$_E$ and R$_F$ are independently selected from the group consisting of hydrogen, alkyl, and cycloalkyl.

8. The compound according to claim 6, wherein R$_C$ is hydrogen; and R$_D$ is heteroarylalkyl.

* * * * *

UNITED STATES PATENT AND TRADEMARK OFFICE
CERTIFICATE OF CORRECTION

PATENT NO. : 7,728,026 B2
APPLICATION NO. : 11/401635
DATED : June 1, 2010
INVENTOR(S) : Zhu et al.

It is certified that error appears in the above-identified patent and that said Letters Patent is hereby corrected as shown below:

On the Title Page
Item (56) OTHER PUBLICATIONS:

Welkin, D., et al., should read as -- Weltin, D., et al.

Signed and Sealed this
Fifth Day of April, 2011

David J. Kappos
*Director of the United States Patent and Trademark Office*